(12) United States Patent
Bertani et al.

(10) Patent No.: US 8,222,266 B2
(45) Date of Patent: *Jul. 17, 2012

(54) AZABICYCLO [3.1.0] HEXYL DERIVATIVES AS MODULATORS OF DOPAMINE D$_3$ RECEPTORS

(75) Inventors: Barbara Bertani, Verona (IT); Anna Checchia, Verona (IT); Romano Di Fabio, Verona (IT); Gabriella Gentile, Verona (IT); Fabrizio Micheli, Verona (IT); Alessandra Pasquarello, Verona (IT); Silvia Terreni, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 574 days.

This patent is subject to a terminal disclaimer.

(21) Appl. No.: 12/295,304

(22) PCT Filed: Mar. 30, 2007

(86) PCT No.: PCT/EP2007/053117
§ 371 (c)(1),
(2), (4) Date: Oct. 21, 2009

(87) PCT Pub. No.: WO2007/113260
PCT Pub. Date: Oct. 11, 2007

(65) Prior Publication Data
US 2010/0069416 A1    Mar. 18, 2010

(30) Foreign Application Priority Data

Apr. 3, 2006  (GB) .................................. 0607892.7
Feb. 21, 2007  (GB) .................................. 0703397.0

(51) Int. Cl.
C07D 403/06 (2006.01)
A61K 31/513 (2006.01)

(52) U.S. Cl. ........................................ 514/274; 544/315
(58) Field of Classification Search .................. 544/315; 514/274
See application file for complete search history.

(56) References Cited

U.S. PATENT DOCUMENTS

| | | | |
|---|---|---|---|
| 6,204,284 B1 | 3/2001 | Beer et al. | 514/412 |
| 7,727,988 B2 * | 6/2010 | Bertani et al. | 514/252.02 |
| 2007/0142438 A1 | 6/2007 | Arista et al. | 514/341 |
| 2007/0249642 A1 | 10/2007 | Bertani et al. | 514/269 |
| 2008/0058398 A1 | 3/2008 | Anderton et al. | 514/374 |
| 2008/0167357 A1 | 7/2008 | Hamprecht et al. | 514/384 |
| 2008/0176917 A1 | 7/2008 | Andreotti et al. | 514/384 |
| 2008/0227837 A1 | 9/2008 | Arista et al. | 514/384 |
| 2008/0242715 A1 | 10/2008 | Capelli et al. | 514/384 |
| 2009/0030062 A1 | 1/2009 | Gentile et al. | 514/412 |
| 2009/0036461 A1 | 2/2009 | Hamprecht et al. | 514/252.06 |
| 2009/0124629 A1 | 5/2009 | Bonanomi et al. | 514/252.06 |
| 2009/0221593 A1 | 9/2009 | Bonanomi et al. | 514/249 |
| 2009/0221618 A1 | 9/2009 | Arista et al. | 514/274 |

FOREIGN PATENT DOCUMENTS

| | | |
|---|---|---|
| DE | 43 38 396 | 5/1995 |
| WO | WO 2006/108701 | 10/2006 |
| WO | WO 2006/133946 | 12/2006 |

OTHER PUBLICATIONS

Le Foll et al., PubMed Abstract (Expert Opinion Investig Drugs, 16(1):45-57), Jan. 2007.*
Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*
U.S. Appl. No. 11/917,352, filed Jun. 13, 2006, Arista, et al.
U.S. Appl. No. 12/295,024, filed Mar. 30, 2007, Bertani, et al.

* cited by examiner

*Primary Examiner* — Deepak Rao
(74) *Attorney, Agent, or Firm* — Bonnie L. Deppenbrock

(57) ABSTRACT

The present invention relates to certain azabicyclo compounds of formula (I)':

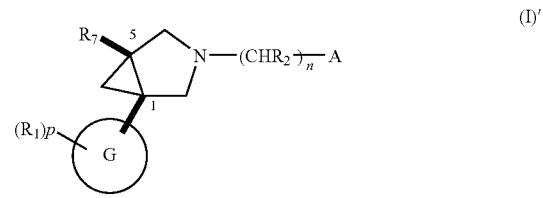

wherein the various groups are defined herein and that are modulators of dopamine D$_3$ receptors, e.g. to treat drug dependency, as antipsychotic agents, to treat obsessive compulsive spectrum disorders, or premature ejaculation.

7 Claims, No Drawings

AZABICYCLO [3.1.0] HEXYL DERIVATIVES AS MODULATORS OF DOPAMINE $D_3$ RECEPTORS

This application is a 371 of International Application No. PCT/EP2007/053117 filed 30 Mar. 2007, this application claims the priority of GB 0607892.7 filed 3 Apr. 2006 and GB 0703397.0 filed 21 Feb. 2007 which are incorporated herein in their entirety.

The present invention relates to novel compounds, processes for their preparation, intermediates used in these processes, pharmaceutical compositions containing them and their use in therapy, as modulators of dopamine $D_3$ receptors.

Recently a patent application has been published as WO2005/080382 and discloses the compounds of the following formula or salts thereof:

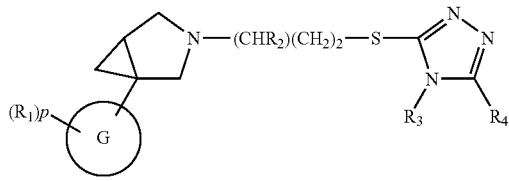

wherein
- G is selected from a group consisting of: phenyl, pyridyl, benzothiazolyl, indazolyl;
- p is an integer ranging from 0 to 5;
- $R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl; or corresponds to a group $R_5$;
- $R_2$ is hydrogen or $C_{1-4}$alkyl;
- $R_3$ is $C_{1-4}$alkyl;
- $R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, halo$C_{1-4}$alkyl, $C_{1-4}$alkoxy, $C_{1-4}$alkanoyl;
- $R_5$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;

and when $R_1$ is chlorine and p is 1, such $R_1$ is not present in the ortho position with respect to the linking bond to the rest of the molecule; and when $R_1$ corresponds to $R_5$, p is 1.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

The present invention provides a compound of formula (I) or a pharmaceutically acceptable salt thereof:

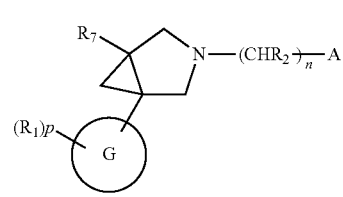

(I)

wherein
- G is selected from a group consisting of: phenyl, a 5- or 6-membered monocyclic heteroaryl group, or a 8- to 11-membered heteroaryl bicyclic group;
- A is a group P wherein
P is

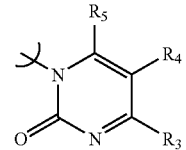

- p is an integer ranging from 0 to 5;
- $R_1$ is halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_6$; and when p is an integer ranging from 2 to 5, each $R_1$ may be the same or different;
- $R_2$ is hydrogen or $C_{1-4}$alkyl;
- n is 4, 5 or 6;
- $R_3$ is selected in the group consisting of: hydrogen, halogen, cyano, $C_{1-4}$alkyl, $C_{3-7}$ cycloalkyl, halo$C_{1-4}$alkyl, $C_{1-4}$alkoxy, halo$C_{1-4}$alkoxy, $C_{1-4}$alkanoyl and NR'R"; or $R_3$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl, $SF_5$ and halo$C_{1-4}$alkoxy; and wherein such halo$C_{1-4}$alkoxy substituents, wherein placed in adjacent positions, may for, together with the carbon atoms to which they're attached a 5, 6-membered unsaturated heterocyclic ring;
- $R_4$ is selected in the group consisting of: hydrogen, halogen, hydroxy, cyano, $C_{1-4}$alkyl, $C_{3-7}$ cycloalkyl, halo$C_{1-4}$ alkyl, $C_{1-4}$alkoxy, halo$C_{1-4}$alkoxy, $C_{1-4}$alkanoyl and NR'R"; or $R_4$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl and $SF_5$;
- $R_5$ is selected in the group consisting of: hydrogen, halogen, hydroxy, cyano, $C_{1-4}$alkyl, $C_{3-7}$ cycloalkyl, halo$C_{1-4}$ alkyl, $C_{1-4}$alkoxy, halo$C_{1-4}$alkoxy, $C_{1-4}$alkanoyl and NR'R"; or $R_5$ is a phenyl group, a 5-14 membered heterocyclic group; and any of such phenyl or heterocyclic group is optionally substituted by 1, 2, 3 or 4 substituents selected from the group consisting of: halogen, cyano, halo$C_{1-4}$alkyl, $C_{1-4}$alkoxy, $C_{1-4}$alkanoyl and $SF_5$;

$R_6$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such $R_6$ group is optionally substituted by one or two substituents selected from: halogen, cyano, $C_{1-4}$alkyl, halo$C_{1-4}$alkyl, $C_{1-4}$alkoxy, $C_{1-4}$alkanoyl;

$R_7$ is hydrogen or $C_{1-2}$alkyl;

R' is H, $C_{1-4}$alkyl or $C_{1-4}$alkanoyl;

R" is defined as R';

R' and R" taken together with the interconnecting nitrogen atom may form a 5-, 6-membered saturated or unsaturated heterocyclic ring;

wherein at least one of $R_4$ and $R_5$ is hydrogen; and wherein only one $R_2$ group ma be different from hydrogen.

Because of the presence of the fused cyclopropane, compounds of formula (I) are believed to have a "cis" disposition of the substituents (both groups linked to the bicyclic ring system are on the same face of this bicyclic ring system).

In one embodiment of the present invention compounds of formula (I)' are provided which correspond to the compounds of formula (I), or salts thereof, having "cis" disposition, represented by the bold highlight of the bonds

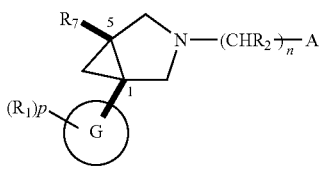

(I)' wherein G, A, p, n, $R_1$, $R_2$, and $R_7$ are defined as above for compounds of formula (I).

It will be appreciated that compounds of formula (I)' possess at least two chiral centres, namely at position 1 and 5 in the 3-azabicyclo[3.1.0]hexane portion of the molecule. Because of the fixed cis disposition, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In compounds of formula (I)' there are at least two chiral centres, which are located in the cyclopropane portion, as depicted below (the bold highlight of the bonds means the "cis" configuration); through optical resolution of a mixture containing the two stereoisomers which are enantiomers with respect to the chiral centres in the cyclopropane, single stereoisomers of compounds of formula (I)' may be obtained as shown in the scheme below:

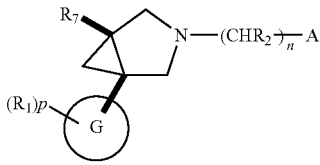

(I)'

↓ Resolution

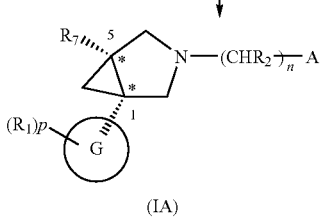

(IA)

Absolute configuration of chiral center at position named 1 and 5 may be assigned using Cahn-Ingold-Prelog nomenclature based on groups' priorities.

In one embodiment of the present invention compounds of formula (IA) are provided that correspond to stereochemical isomers of compounds of formula (I)', enriched in configuration shown in the picture below at chiral centers at position named 1 and 5:

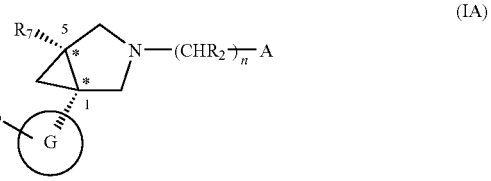

(IA)

wherein G, A, p, n, $R_1$, $R_2$, and $R_7$ are defined as above for compounds of formula (I), or a salt thereof.

It is intended in the context of the present invention that stereochemical isomers of formula (IA) enriched in one configuration at centers named 1 and 5, correspond in one embodiment to at least 90% e.e. (enantiomeric excess). In another embodiment the isomers correspond to at least 95% e.e. In another embodiment the isomers correspond to at least 99% e.e.

In another embodiment of the present invention compounds of formula (IH) are provided that correspond to stereochemical isomers of compounds of formula (I)', enriched in configuration (1S,5R) or (1R,5R)

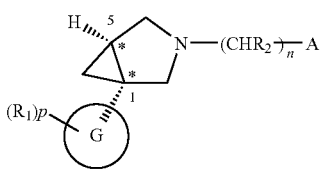

(IH)

wherein G, A, p, n, $R_1$ and $R_2$ are defined as above for compounds of formula (I) and $R_7$ is hydrogen, or a salt thereof.

Different nomenclature for absolute configuration assigned to chiral center named 1 [(1R) or (1S)] may be generated by different meanings for G group.

For example, when the group G is a phenyl group, absolute configuration nomenclature for compounds of formula (IH) is (1S,5R).

It is intended in the context of the present invention that stereochemical isomers enriched in configuration (1S,5R) or (1R,5R) of formula (IH) correspond in one embodiment to at least 90% e.e. (enantiomeric excess). In another embodiment the isomers correspond to at least 95% e.e. In another embodiment the isomers correspond to at least 99% e.e.

In another embodiment of the present invention the stereochemical isomers enriched in configuration (1R,5S) are provided.

In another embodiment of the present invention compounds of formula (IL) are provided that correspond to stereochemical isomers of compounds of formula (I)', enriched in configuration shown in the picture below at chiral centers at position named 1 and 5:

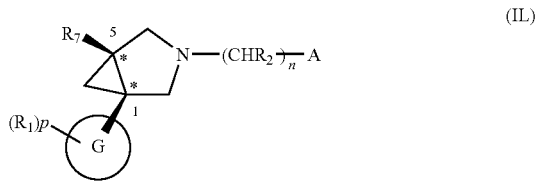

wherein G, A, p, n, $R_1$, $R_2$ and $R_7$ are defined as above for compounds of formula (I), or a salt thereof.

The term '$C_{1-4}$alkyl' as used herein as a group or a part of the group refers to a linear or branched alkyl group containing from 1 to 4 carbon atoms; examples of such groups include methyl, ethyl, propyl, isopropyl, n-butyl, isobutyl, tert butyl.

The term '$C_{3-7}$ cycloalkyl group' as used herein means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term '$C_{1-4}$ alkoxy group' as used herein may be a linear or a branched chain alkoxy group, for example methoxy, ethoxy, propoxy, prop-2-oxy, butoxy, but-2-oxy or methylprop-2-oxy and the like.

The term '$C_{1-4}$ alkanoyl group' as used herein may be a linear or a branched chain alkanoyl group, for example acetyl, ethylcarbonyl, n-propylcarbonyl, i-propyl carbonyl, n-butylcarbonyl or t-butylcarbonyl and the like.

The term 'halogen' as used herein refers to a fluorine, chlorine, bromine or iodine atom.

The term 'halo $C_{1-4}$alkyl' as used herein means an alkyl group having one or more carbon atoms and wherein at least one hydrogen atom is replaced with halogen such as for example a trifluoromethyl group and the like.

The term 'halo $C_{1-4}$alkoxy group' as used herein may be a $C_{1-4}$alkoxy group as defined before substituted with at least one halogen, preferably fluorine, such as $OCHF_2$, or $OCH_2F$ or $OCF_3$.

The term 'aryl' as used herein means an aromatic carbocyclic moiety such as phenyl, biphenyl or naphthyl.

The term '5,6-membered monocyclic heteroaryl' as used herein means an aromatic monocyclic heterocycle ring of 5 or 6 members and having at least one heteroatom selected from nitrogen, oxygen and sulfur, and containing at least 1 carbon atom.

Representative 5, 6 membered monocyclic heteroaryl groups include (but are not limited to): furyl, thiophenyl, pyrrolyl, pyridyl, oxazolyl, isooxazolyl, pyrazolyl, imidazolyl, thiazolyl, isothiazolyl, pyridazinyl, pyrimidinyl, pyrazinyl, triazinyl, triazolyl and tetrazolyl.

The term '8, 11-membered bicyclic heteroaryl' as used herein means an aromatic bicyclic heterocycle ring of 8 to 11 members and having at least one heteroatom selected from nitrogen, oxygen and sulfur, and containing at least 1 carbon atom.

Representative 8, to 11 membered bicyclic heteroaryl groups include (but are not limited to): benzofuranyl, benzothiophenyl, indolyl, isoindolyl, azaindolyl, quinolinyl, isoquinolinyl, benzoxazolyl, benzimidazolyl, benzothiazolyl, quinazolinyl and phthalazinyl.

The term 5-14 membered heterocycle means a 5 to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

In one embodiment, $R_1$ is halogen, cyano, acetyl, trifluoromethyl, trifluoromethoxy.

In one embodiment, $R_2$ is hydrogen. In another embodiment $R_2$ is $C_{1-4}$alkyl (e.g. methyl).

In one embodiment R$_3$ may be hydrogen, C$_{1-4}$alkyl, haloC$_{1-4}$alkyl, C$_{1-4}$alkoxy, haloC$_{1-4}$alkoxy, C$_{1-4}$alkanoyl, hydroxyl, phenyl or halogen.

In one embodiment R$_4$ may be hydrogen, C$_{1-4}$alkyl, haloC$_{1-4}$alkyl, C$_{1-4}$alkoxy, haloC$_{1-4}$alkoxy, C$_{1-4}$alkanoyl, halogen, phenyl or hydroxyl.

In one embodiment R$_5$ may be hydrogen, C$_{1-4}$alkyl, haloC$_{1-4}$alkyl, C$_{1-4}$alkoxy, haloC$_{1-4}$alkoxy, C$_{1-4}$alkanoyl, phenyl, hydroxyl or halogen.

In one embodiment, R$_6$ is a group selected from: isoxazolyl, 2-pyrrolidinonyl, —CH$_2$—N-pyrrolyl, 1,1-dioxido-2-isothiazolidinyl, 2-thienyl, 2-pyridyl, 2-thiazolyl which is optionally substituted by one or two substituents selected from: halogen, cyano, C$_{1-2}$alkyl (e.g. methyl), haloC$_{1-2}$alkyl (e.g. trifluoromethyl), C$_{1-2}$alkoxy (e.g. methoxy), C$_{1-3}$alkanoyl (e.g. acetyl).

In one embodiment R$_7$ is hydrogen or methyl.

In another embodiment R$_2$ is hydrogen.

In one embodiment, p is 0, 1 or 2.

In another embodiment, p is 1.

In one embodiment, G is a phenyl group.

In another embodiment R$_1$ trifluoromethyl.

In one embodiment n is 3 or 4.

In one embodiment n is 4, 5 or 6. In another embodiment n is 4.

In another embodiment R$_3$ and R$_4$ are hydrogen, methyl, hydroxyl, phenyl or fluorine.

In one embodiment R$_3$ may be hydrogen, an optionally substituted phenyl, methyl, a optionally substituted pyridyl, an optionally substituted isooxazolyl or an optionally substituted thiazolyl.

In one embodiment, R$_4$ is hydrogen or methyl.

In another embodiment R$_5$ is hydrogen.

In another embodiment R$_6$ is isoxazolyl, 2-pyrrolidinonyl, -1,1-dioxido-2-isothiazolidinyl.

In another embodiment R$_7$ is hydrogen.

In one embodiment, a compound of formula (IB) or a salt thereof is provided, wherein R$_1$, R$_2$, R$_3$, R$_4$, R$_5$, p, n and R$_7$ are as defined for formula (I):

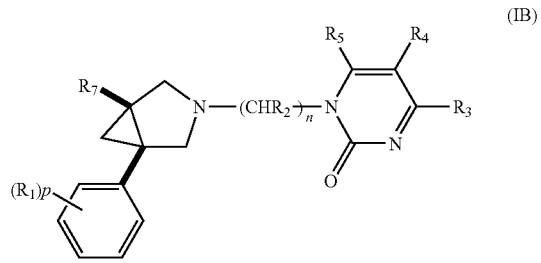

(IB)

In Formula (IB), in one embodiment, n is 4, p is 1, R$_1$ is trifluoromethyl, R$_2$ is hydrogen, R$_3$ and R$_4$ may be hydrogen, methyl, hydroxyl, phenyl or fluorine, R$_5$ is hydrogen and R$_7$ is hydrogen.

In Formula (IB), in one embodiment, n is 4, p is 1, R$_1$ is trifluoromethyl, R$_2$ is hydrogen, R$_4$ may be hydrogen or methyl, R$_3$ may be hydrogen, an optionally substituted phenyl, methyl, a optionally substituted pyridyl, an optionally substituted isooxazolyl or an optionally substituted thiazolyl, R$_5$ is hydrogen and R$_7$ is hydrogen.

In Formula (IB), in one embodiment, n is 4, p is 1, R$_1$ is trifluoromethyl, R$_2$ is hydrogen, R$_4$ may be hydrogen, methyl or phenyl, R$_3$ may be hydrogen, an optionally substituted phenyl, methyl, a optionally substituted pyridyl, an optionally substituted isooxazolyl or an optionally substituted thiazolyl, R$_5$ is hydrogen and R$_7$ is hydrogen.

The absolute configuration of the compounds of the present invention was may be assigned in agreement with the method described in the PCT International Publication WO2005/080382.

Further embodiments of the present invention are compounds of formula (IB)' which correspond to the stereochemical isomers of compounds of formula (IB) as defined above enriched in configuration (1 S,5R).

In one embodiment, a stereochemical isomer enriched in the (1S,5R) configuration of formula (IB)' or a salt thereof is provided, wherein R$_1$, R$_2$, R$_3$, R$_4$, R$_5$, p, n and R$_7$ are as defined for formula (I):

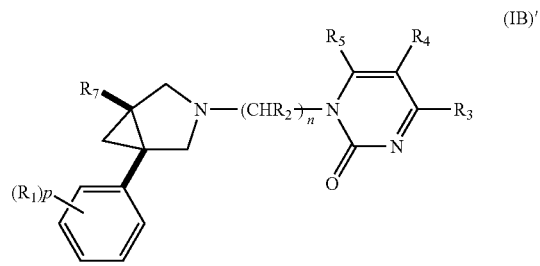

(IB)'

In Formula (IB)', in one embodiment, n is 4, p is 1, R$_1$ is trifluoromethyl, R$_2$ is hydrogen, R$_3$ and R$_4$ may be hydrogen, methyl, hydroxyl, phenyl or fluorine, R$_5$ is hydrogen and R$_7$ is hydrogen.

In Formula (IB)', in one embodiment, n is 4, p is 1, R$_1$ is trifluoromethyl, R$_2$ is hydrogen, R$_4$ may be hydrogen or methyl, R$_3$ may be hydrogen, an optionally substituted phenyl, methyl, a optionally substituted pyridyl, an optionally substituted isooxazolyl or an optionally substituted thiazolyl, R$_5$ is hydrogen and R$_7$ is hydrogen.

In Formula (IB)', in one embodiment, n is 4, p is 1, R$_1$ is trifluoromethyl, R$_2$ is hydrogen, R$_4$ may be hydrogen, methyl or phenyl, R$_3$ may be hydrogen, an optionally substituted phenyl, methyl, a optionally substituted pyridyl, an optionally substituted isooxazolyl or an optionally substituted thiazolyl, R$_5$ is hydrogen and R$_7$ is hydrogen.

Certain of the compounds of the invention may form acid addition salts with one or more equivalents of the acid. The present invention includes within its scope all possible stoichiometric and non-stoichiometric forms.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Hereinafter, compounds of formula (I) and their pharmaceutically acceptable salts, solvates and prodrugs defined in any aspect of the invention (except intermediate compounds in chemical processes) are referred to as "compounds of the invention".

Those skilled in the art will appreciate that in the preparation of the compounds of the invention, it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

The present invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and non-pharmaceutically acceptable salts thereof that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of the present invention and non-pharmaceutically acceptable salts thereof can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

In one embodiment, example compounds of the invention include:

4-phenyl-1-(4-{(1S,5R)-1-[4-(trifluoromethyl)phenyl]-3-azabicyclo[3.1.0]hex-3-yl}butyl)-2(1H)-pyrimidinone;

4-methyl-1-(4-{(1S,5R)-1-[4-(trifluoromethyl)phenyl]-3-azabicyclo[3.1.0]hex-3-yl}butyl)-3,4-dihydro-2(1H)-pyrimidinone;

or a pharmaceutically acceptable salt thereof.

In another embodiment, example compounds of the invention include:

5-phenyl-1-(4-{(1S,5R)-1-[4-(trifluoromethyl)phenyl]-3-azabicyclo[3.1.0]hex-3-yl}butyl)-2(1H)-pyrimidinone;

4-(2,4-dimethyl-1,3-thiazol-5-yl)-1-(4-{(1S,5R)-1-[4-(trifluoromethyl)phenyl]-3-azabicyclo[3.1.0]hex-3-yl}butyl)-2(1H)-pyrimidinone;

4-(3-pyridinyl)-1-(4-{(1S,5R)-1-[4-(trifluoromethyl)phenyl]-3-azabicyclo[3.1.0]hex-3-yl}butyl)-2(1H)-pyrimidinone;

4-(2-fluorophenyl)-1-(4-{(1S,5R)-1-[4-(trifluoromethyl)phenyl]-3-azabicyclo[3.1.0]hex-3-yl}butyl)-2(1H)-pyrimidinone;

4-(3,5-dimethyl-4-isoxazolyl)-1-(4-{(1S,5R)-1-[4-(trifluoromethyl)phenyl]-3-azabicyclo[3.1.0]hex-3-yl}butyl)-2(1H)-pyrimidinone;

4-(2-methyl-4-pyridinyl)-1-(4-{(1S,5R)-1-[4-(trifluoromethyl)phenyl]-3-azabicyclo[3.1.0]hex-3-yl}butyl)-2(1H)-pyrimidinone;

4-(2-methyl-3-pyridinyl)-1-(4-{(1S,5R)-1-[4-(trifluoromethyl)phenyl]-3-azabicyclo[3.1.0]hex-3-yl}butyl)-2(1H)-pyrimidinone;

4-(2,2-difluoro-1,3-benzodioxol-4-yl)-1-(4-{(1S,5R)-1-[4-(trifluoromethyl)phenyl]-3-azabicyclo[3.1.0]hex-3-yl}butyl)-2(1H)-pyrimidinone;

4-(6-methyl-2-pyridinyl)-1-(4-{(1S,5R)-1-[4-(trifluoromethyl)phenyl]-3-azabicyclo[3.1.0]hex-3-yl}butyl)-2(1H)-pyrimidinone;

5-methyl-4-(3-pyridinyl)-1-(4-{(1S,5R)-1-[4-(trifluoromethyl)phenyl]-3-azabicyclo[3.1.0]hex-3-yl}butyl)-2(1H)-pyrimidinone;

4-methyl-1-(4-{(1S,5R)-1-[4-(trifluoromethyl)phenyl]-3-azabicyclo[3.1.0]hex-3-yl}butyl)-3,4-dihydro-2(1H)-pyrimidinone;

4-phenyl-1-(4-{(1S,5R)-1-[4-(trifluoromethyl)phenyl]-3-azabicyclo[3.1.0]hex-3-yl}butyl)-2(1H)-pyrimidinone;

or a pharmaceutically acceptable salt thereof.

In another embodiment, the compounds of formula (I) are selected from the group consisting of hydrochloride salts, of the compounds listed below:

5-phenyl-1-(4-{(1S,5R)-1-[4-(trifluoromethyl)phenyl]-3-azabicyclo[3.1.0]hex-3-yl}butyl)-2(1H)-pyrimidinone;

4-(2,4-dimethyl-1,3-thiazol-5-yl)-1-(4-{(1S,5R)-1-[4-(trifluoromethyl)phenyl]-3-azabicyclo[3.1.0]hex-3-yl}butyl)-2(1H)-pyrimidinone;

4-(3-pyridinyl)-1-(4-{(1S,5R)-1-[4-(trifluoromethyl)phenyl]-3-azabicyclo[3.1.0]hex-3-yl}butyl)-2(1H)-pyrimidinone;

4-(2-fluorophenyl)-1-(4-{(1S,5R)-1-[4-(trifluoromethyl)phenyl]-3-azabicyclo[3.1.0]hex-3-yl}butyl)-2(1H)-pyrimidinone;

4-(3,5-dimethyl-4-isoxazolyl)-1-(4-{(1S,5R)-1-[4-(trifluoromethyl)phenyl]-3-azabicyclo[3.1.0]hex-3-yl}butyl)-2(1H)-pyrimidinone;

4-(2-methyl-4-pyridinyl)-1-(4-{(1S,5R)-1-[4-(trifluoromethyl)phenyl]-3-azabicyclo[3.1.0]hex-3-yl}butyl)-2(1H)-pyrimidinone;

4-(2-methyl-3-pyridinyl)-1-(4-{(1S,5R)-1-[4-(trifluoromethyl)phenyl]-3-azabicyclo[3.1.0]hex-3-yl}butyl)-2(1H)-pyrimidinone;

4-(2,2-difluoro-1,3-benzodioxol-4-yl)-1-(4-{(1S,5R)-1-[4-(trifluoromethyl)phenyl]-3-azabicyclo[3.1.0]hex-3-yl}butyl)-2(1H)-pyrimidinone;

4-(6-methyl-2-pyridinyl)-1-(4-{(1S,5R)-1-[4-(trifluoromethyl)phenyl]-3-azabicyclo[3.1.0]hex-3-yl}butyl)-2(1H)-pyrimidinone;

5-methyl-4-(3-pyridinyl)-1-(4-{(1S,5R)-1-[4-(trifluoromethyl)phenyl]-3-azabicyclo[3.1.0]hex-3-yl}butyl)-2(1H)-pyrimidinone;

4-methyl-1-(4-{(1S,5R)-1-[4-(trifluoromethyl)phenyl]-3-azabicyclo[3.1.0]hex-3-yl}butyl)-3,4-dihydro-2(1H)-pyrimidinone;

4-phenyl-1-(4-{(1S,5R)-1-[4-(trifluoromethyl)phenyl]-3-azabicyclo[3.1.0]hex-3-yl}butyl)-2(1H)-pyrimidinone.

Some of the compounds of the present invention may be prepared following some of the procedures described in PCT International Publication WO2005/080382.

The present invention also provides a process for preparing a compound of formula (I)' or a salt thereof as defined above, which comprises the steps of:

a) reacting a compound of formula (II):

$$\text{(II)}$$

wherein $R_1$, $R_7$ and p are as defined for formula (I), with a compound of formula (III):

$$X-(CHR_2)_n-A \quad \text{(III)}$$

wherein $R_2$, A and n are as defined for formula (I) and X is a leaving group,

Or b) reacting a compound of formula (II) as above defined:

$$\text{(II)}$$

with a compound of formula (IV)

$$\text{(IV)}$$

$$R_2 \overset{O}{\underset{}{\parallel}} (CHR_2)_{n-1}-A$$

wherein $R_2$, A and n are as defined for formula (I);

and thereafter optionally for process (a) or process (b):

(i) removing any protecting group(s); and/or (ii) forming a salt; and/or (iii) converting a compound of formula (I)' or a salt thereof to another compound of formula (I)' or a salt thereof.

Process (a) may be performed using conventional methods for the formation of a tertiary amine. The leaving group X can be halogen such as chlorine. Alternatively X can be a sulfonyloxy group such $C_{1-2}$ alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When X is a halogen the reaction may be carried out using a base such as potassium carbonate in the presence of a source of iodide such as sodium iodide in a solvent such as N,N-dimethylformamide at a suitable temperature, e.g. 60° C.

Process (b) may be performed using conventional methods for the formation of a tertiary amine by means of reductive ammination. For example when, for compounds of formula (IV) $R_2$ is hydrogen, the reaction may be carried out using sodium triacetoxy borohydride in a suitable solvent such as 1,2 dichloroethane at 0° C.

In another embodiment the present invention provides a process for the preparation of compounds of formula (Ia), i.e. a compound of formula (I)' wherein p is 1 or 2 and one $R_1$ is a group $R_6$, comprises the following steps:
c) reacting a compound of formula (V):

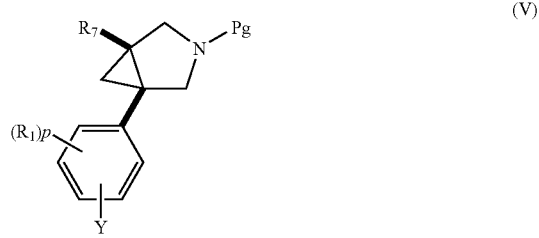

wherein $R_1$, and $R_7$ are as defined for formula (I), Pg is a suitable amine protecting group such as for example tert-buthoxy carbonyl group, p is 0 or 1 and Y is halogen, a perfluoroalkylsulfonyloxy group (e.g. trifluoromethylsulfonyloxy), or Y is a group M selected from a boron derivative (e.g. a boronic acid function $B(OH)_2$) or a metal function such as trialkylstannyl (e.g. $SnBu_3$), zinc halide or magnesium halide; with a compound of formula $R_6$—$Y_1$, wherein $R_6$ is an optionally substituted isoxazolyl, thienyl, thiazolyl or pyridyl, group, $Y_1$ is halogen when Y is a group M; or, when Y is halogen or a perfluoroalkylsulfonyloxy group, $Y_1$ is a group M as defined above or hydrogen that can be activated by a suitable base (e.g. $Cs_2CO_3$) in the presence of a suitable transition metal (e.g. Pd); "leaving group" is as understood by a skilled chemist, i.e. a group which can be displaced by a nucleophile in e.g. a $S_N2$, $S_N1$ or $S_NAr$ type reaction; to form a compound of formula (XXXIV)

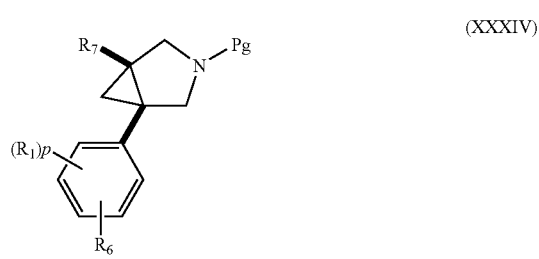

wherein $R_1$, and $R_7$ are as defined for formula (I), Pg is a suitable amine protecting group such as for example tert-buthoxy carbonyl group, p is 0 or 1 and $R_6$ is an optionally substituted isoxazolyl, thienyl, thiazolyl or pyridyl, group;
d) removing the Pg group;
e) reacting the obtained product with a compound of formula (III) or (IV), as above defined, under the conditions described for processes a) or b);
and thereafter optionally:
(i) removing any protecting group(s); and/or
(ii) forming a salt; and/or
(iii) converting a compound of formula (Ia) or a salt thereof to another compound of formula (Ia) or a salt thereof.

Reaction of a compound of formula (V) with $R_1$—$Y_1$ according to process (c) may be effected in the presence of a transition metal e.g., palladium catalyst such as bis-triphenylphosphinepalladium dichloride, tetrakis-triphenylphosphinepalladium (0) or the complex formed in situ from tris(dibenzylideneacetone) dipalladium(0) and 4,5-bis(diphenylphosphino)-9,9-dimethylxanthene. When M is a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. When M is hydrogen that can be activated by a suitable base (e.g. $Cs_2CO_3$) in the presence of a suitable transition metal (e.g. Pd) the reaction may be carried out in an inert solvent such as dioxane in the presence of a suitable base such as $Cs_2CO_3$. The substituent Y may be halogen such as bromine, or a sulfonyloxy group such as trifluoromethylsulfonyloxy; and $Y_1$ is may be a group M, such as hydrogen that can be activated by a suitable base (e.g. $Cs_2CO_3$) in the presence of a suitable transition metal (e.g. Pd).

Compounds of formula (II) may be prepared by methods well known in the art (e.g. *J. Med. Chem.* 1981, 24, 481-490 or PCT International Publication WO2005/080382). Interconversion of groups $R_1$ may be affected by methodology well known in the art (e.g. demethylation of a methoxy group resulting in a hydroxy group using a suitable Lewis acidic reagent such as boron tribromide in an inert solvent such as dichloromethane).

In one aspect of the present invention there is provided a process for the preparation of compounds of formula (IIa), i.e. a compound of general formula (II) wherein $R_7$ is hydrogen and G is a phenyl ring and $R_1$ is defined as for compounds of formula (I).

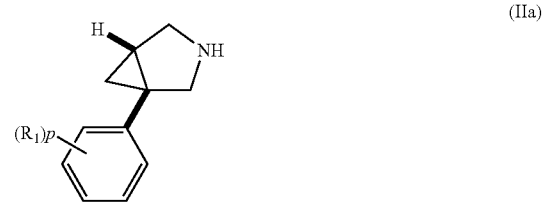

The process may be conveniently performed also for preparing compounds of formula (IIb), wherein the phenyl moiety of compound (IIa) is replaced by pyridine. This process comprises the following steps:

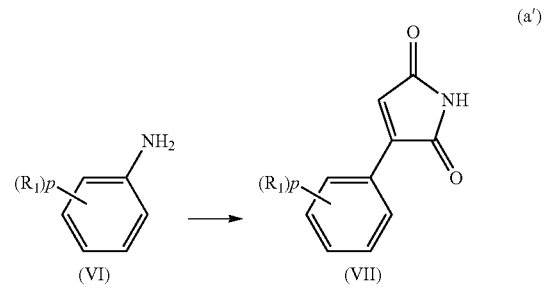

In another aspect of the present invention an alternative synthetic process for the preparation of compounds of formula (II), is provided. This process comprises the following steps:

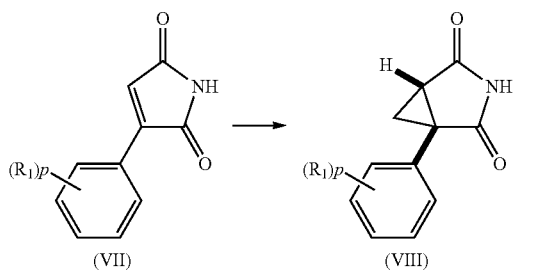

(b')

(VII) → (VIII)

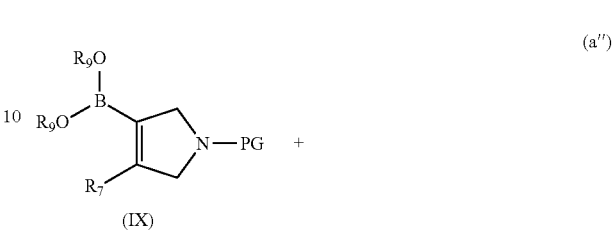

(a")

(IX)

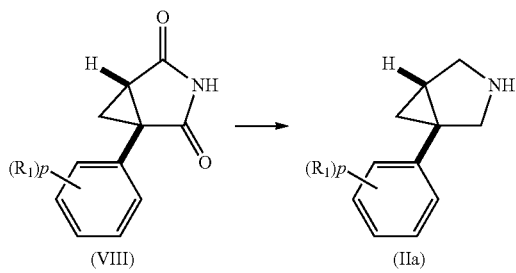

(c')

(VIII) → (IIa)

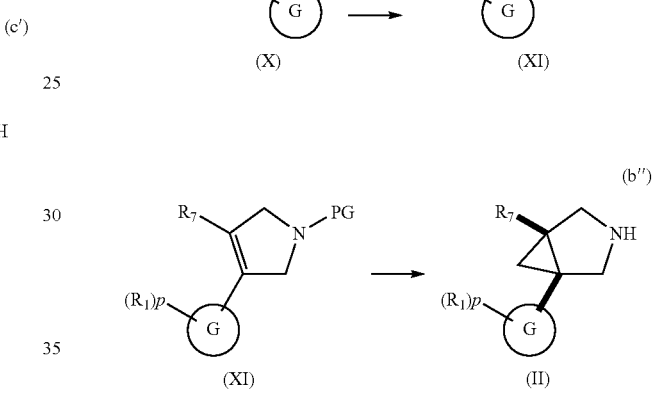

(b")

wherein:

step (a') means diazotation of an aniline (VI) followed by reaction with maleimide to give 3-arylmaleimide (VII);

step (b') means cycloropanation of (VII) to provide bicyclic imide (VIII);

step (c') means reduction of imide (VIII) to give compounds of formula (IIIa).

Step (a') may be effected using conventional methods for the Meerwein reaction (e.g. *J. Am. Chem. Soc.* 1955, 77, 2313 describes the formation of arylmaleimides using this approach). Alternatively, in many cases this step is suitably performed applying a procedure where to a mixture of maleimide, an appropriate copper (II) salt such as anhydrous CuCl$_2$, and a suitable organonitrile, such as tert-butyl nitrite, in a compatible solvent, such as acetonitrile, is slowly added a solution of a compound of formula (VI). This is followed by allowing time to react as appropriate and a suitable workup.

Step (b') consists of slow addition of a solution of purified compound of formula (VII), or mixtures containing a compound of formula (VII), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (c') can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

wherein:
$R_1$, p and G are as defined for formula (I), $R_8O$ is a suitable alkoxy group, PG is an appropriate protecting group and Y may be halogen such as bromine, or a sulfonyloxy group such as trifluoromethylsulfonyloxy and comprising the following steps:

step (a") means coupling reaction of a (2,5-dihydro-1H-pyrrol-3-yl)boronate (IX) with the aromatic halogen or sulfonyloxy derivative (X);

step (b") means cycloropanation of (XI) followed by, if appropriate, deprotection to provide bicyclic amine (II).

Step (a") may be effected using conventional methods for the Suzuki coupling, e.g. using tetrakis(triphenylphosphine) palladium(0) as the source of catalytic palladium(0) in the presence of cesium fluoride in an appropriate solvent such as tetrahydrofuran at a suitable temperature. ($R_8O$)$_2$B may suitably be 4,4,5,5-tetramethyl-1,3,2-dioxaborolan-2-yl and PG benzyl, representing a compound of structure (X) as reported in *Synlett* 2002, 5, 829-831.

Step (b") consists of a cyclopropanation reaction effected for example using the reagent generated from trimethylsulfoxonium iodide and a suitable base such as sodium hydride. This is followed by a deprotection reaction.

In another aspect of the present invention there is provided a synthetic process for the preparation of compounds of formula (IIc), i.e. compounds of general formula (II) wherein $R_7$ is $C_{1-2}$ alkyl and G is a phenyl group. This process comprises the following steps:

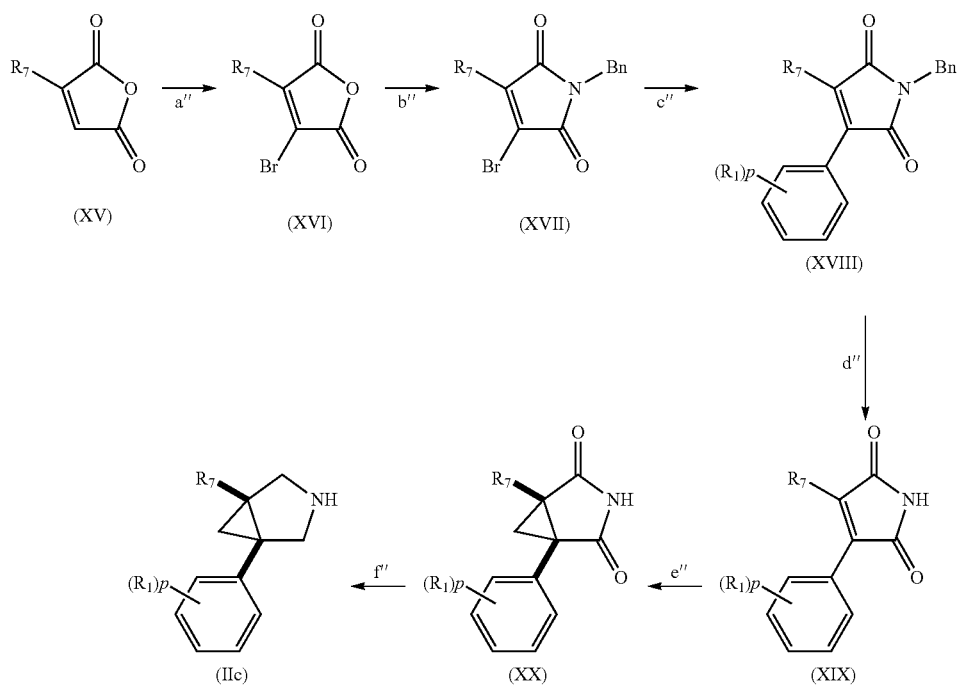

wherein:
step (a") means bromuration of compound (XV) to give compound (XVI);
step (b") means reaction of compound (XVI) with a benzylic amine with a benzylic amine (susceptible to afford benzylic cleavage in acidic conditions) to give imide (XVII);
step (c") means coupling of compound (XVII) with an aryl boronic acid to give compound (XVIII);
step (d") means removal of the benzylic protecting group of compound (XVIII) to give compound (XIX);
step (e") means cyclopropanation of (XIX) to provide bicyclic imide (XX);
step (f") means reduction of imide (XX) to give compounds of formula (IIc).

Step (a') may be effected using bromine in the presence of AlCl3, and heating the mixture at high temperature, suitably 120° C.

Step (b") may be performed heating compound (XVI) together with an appropriate benzylic amine (suitably as 3,4-(dimethoxy)benzylamine or 2,4-(dimethoxy)benzylamine) in the presence of AcONa and AcOH.

Step (c") may be effected using conventional methods for the Suzuki coupling, e.g. using Pd(PPh$_3$)$_2$Cl$_2$ as the source of catalytic palladium(0) in the presence of cesium fluoride, BnEt$_3$NCl and a generic arylboronic acid in an appropriate mixture of solvents, (such as toluene/H$_2$O 1:1) at a suitable temperature (such as 90° C.).

Step (d") may be performed through an appropriate method for acidic cleavage of benzylic protecting group, such as one of those reported in "Protective groups in organic synthesis" by T. W. Greene and P. G. M. Wuts (John Wiley & sons 1991) or "Protecting Groups" by P. J. Kocienski (Georg Thieme Verlag 1994). Suitably, if the benzylic group is represented by 3,4-(dimethoxy)benzyl, protection may be removed through reaction of compound (XVIII) with TFA and anisole in the presence of sulforic acid.

Step (e") consists of slow addition of a solution of purified compound of formula (XIX), or mixtures containing a compound of formula (XIX), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (f") can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

A compound of formula (III), as above defined, may itself be prepared by reacting a compound of formula (XXI):

(XXI)

wherein R$_3$, R$_4$ and R$_5$ are as defined as for formula (I), with a compound of formula (XIII):

L(CHR$_2$)$_n$X         (XIII)

wherein R$_2$ is defined as for formula (I), X is as above defined and L is a leaving group.

The leaving group L can be halogen, such as chlorine. Alternatively L can be a sulfonyloxy group such C$_{1-4}$alkylsulfonyloxy (e.g. methanesulfonyloxy), C$_{1-4}$alkylsulfonyloxy or haloC$_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more C$_{1-2}$alkyl groups; e.g. para-toluenesulfonyloxy. When L is a halogen the reaction may be carried out using a base such as potassium carbonate in the presence of a source of iodide such as sodium iodide in a solvent such as N,N-dimethylformamide at a suitable temperature, e.g. 60° C.

A compound of formula (IV), as above defined, may itself be prepared through the following steps:

f) reacting a compound of formula (XXI):

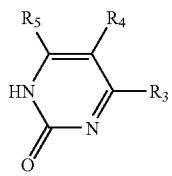

(XXI)

wherein $R_3$, $R_4$ and $R_5$ are as defined as for formula (I), with a compound of formula (XXII)

(XXII)

wherein $R_2$ is defined as for formula (I), X is as above defined and M is an appropriate carbonylic protecting group (for example dimethylacetale or dioxalane);

and then g) cleavage of the protecting group.

Cleavage of the protecting group may be carried out under appropriate conditions known to the man skilled in the art. For example, when M is dimethylacetale, the cleavage may carried out by treatment with a diluted solution of hydrochloric acid in dioxane or methanol under gentle heating (e.g. 60° C.).

A compound of formula (IV), as above defined, may be prepared through the following steps:

h) reacting a compound of formula (XXI), as above defined:

(XXI)

with a compound of formula (XXIII)

NCR$_2$(CHR$_2$)$_{n-1}$X       (XXIII)

wherein $R_2$ is defined as for formula (I), X is as above defined and N is a protected alcoholic function (for example: terbutyldimethylsilyl);

and then i) cleavage of the protecting group under appropriate conditions known to the man skilled in the art and subsequent oxidation of the free alcoholic function obtained to carbonyl group.

For example when N is a terbutyl dimethyl silyl protecting group the cleavage can be performed by treatment with a 1N solution of hydrochloric acid in dioxane at 0° C. for 1 hour. Appropriate conditions for the oxidation step comprise Dess-Martin periodinane mediated oxidation in dry THF as solvent at 0° C. for 1 hour.

Compounds of formula (XIII), (XXII) and (XXIII) are commercially available or may be prepared through reactions known in the literature.

Compounds of formula (XXI) are either commercially available or may be prepared through reactions known in the literature or through the procedures herebelow described.

A suitable synthetic process for the preparation of compounds (XXI), wherein $R_3$, $R_5$ and $R_5$ are as defined as for formula (I), comprises the following steps:

m)

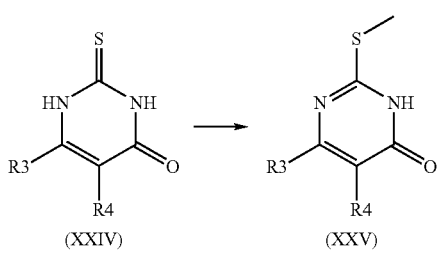

(XXIV)                (XXV)

followed by step n):

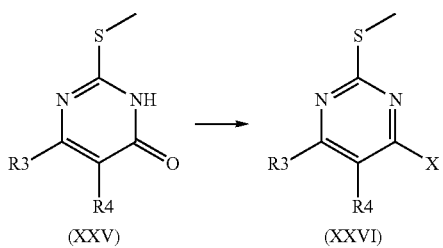

(XXV)                (XXVI)

followed by step o):

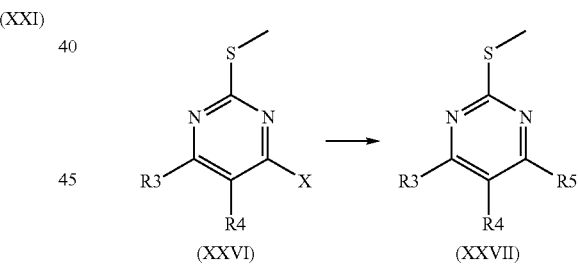

(XXVI)                (XXVII)

followed by step p):

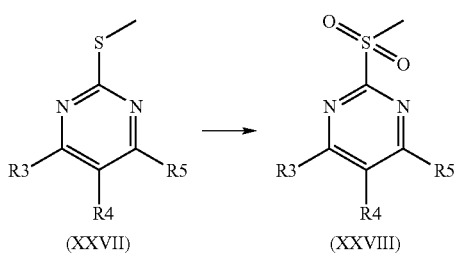

(XXVII)                (XXVIII)

and then by step q):

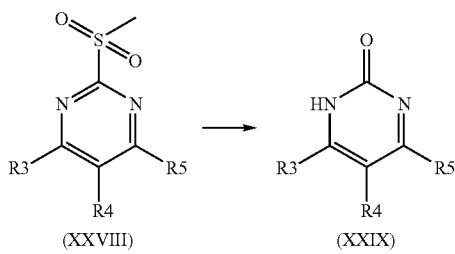

Step m) means sulfur methylation and may be performed starting from compounds of formula (XXIV), wherein R₃ and R₄ are as defined as for formula (I), using MeI in refluxing ethanol as solvent;

Step n) means conversion of the carbonyl group in compounds of formula (XXV), wherein R₃ and R₄ are as defined as for formula (I), into a halogen atom and may be performed for example by using POCl3 in dioxane at reflux;

Step (O) means palladium catalyzed coupling of compounds of formula (XXVI), wherein wherein R₃ and R₄ are as defined as for formula (I) and X is alogen, i.e chlorine or iodine, with the suitable aryl or heteroaryl boronic acids. Step (o) may be performed using conventional method for the Suzuky coupling, using for example Pd(OAc)₂ as the source of catalytic palladium (0), in the presence of Na₂CO₃ as base and a suitable aryl boronic acid or aryl boronic ester in an appropriate solvent, such as nPrOH;

Step p) means oxidation of compounds of formula (XXVII), wherein R₃, R₄ and R₅ are as defined as for formula (I), by means of appropriate oxidative agents such as for example oxone in a suitable solvent i.e. MeOH;

Step q) means basic hydrolysis of the methyl sulphonyl group of compounds of formula (XXVIII), wherein R₃, R₄ and R₅ are as defined as for formula (I), using for example a diluted solution of NaOH at room temperature in dioxane as solvent;

Compounds of formula (XXIV) are either commercially available or may be prepared through reactions known in the literature.

Interconversion reactions between compounds of formula (I)' and salts thereof may be performed using methods well known in the art. Examples include:
(i) converting one or more of R₁ from alkoxy (e.g. methoxy) to hydroxy,
(ii) converting one or more of R₁ from hydroxy to sulfonyloxy, such as alkylsulfonyloxy or haloalkylsulfonyloxy, e.g. methanesulfonyloxy or alkylsulfonyloxy or trifluoro-methanesulfonyloxy,
(iii) converting one or more of R₁ from halogen or perfluoroalkylsulfonyloxy to cyano; and optionally thereafter forming a salt of formula (I)'.

When a specific enantiomer or diastereoisomer of a compound of formula (I) or salts thereof, is required, this may be obtained for example by resolution of a corresponding enantiomeric or diastereosiomeric mixture using conventional methods.

Thus, for example, specific enantiomers or diastereoisomers of the compounds may be obtained from the corresponding enantiomeric or diastereoisomeric mixture using chiral chromatographic methods such as for example chiral HPLC.

Alternatively a specific enantiomer or diastereoisomer of a compound of general formula (I), or salts thereof, may be synthesised from the appropriate optically active intermediates using any of the general processes described herein.

Compounds of formula (I) or pharmaceutically acceptable salts thereof, have been found to exhibit affinity for dopamine receptors, in particular the D₃ receptor, and are expected to be useful in the treatment of disease states which require modulation of such receptors, such as psychotic conditions.

Many of the compounds of formula (I) or pharmaceutically acceptable salts thereof have also been found to have greater affinity for dopamine D₃ than for D₂ receptors. The therapeutic effect of currently available antipsychotic agents (neuroleptics) is generally believed to be exerted via blockade of D₂ receptors; however this mechanism is also thought to be responsible for undesirable extrapyramidal side effects (eps) associated with many neuroleptic agents. It has been suggested that blockade of the recently characterised dopamine D₃ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of formula (I) or salts thereof are provided which have higher (e.g. ≧10× or ≧100× higher) affinity for dopamine D₃ than dopamine D₂ receptors (such affinity can be measured using standard methodology—see herein).

Compounds of the invention may suitably be used as selective modulators of D₃ receptors.

From the localisation of D₃ receptors, it could also be envisaged that the compounds could also have utility for the treatment of substance abuse where it has been suggested that D₃ receptors are involved (e.g. see Levant, 1997, Pharmacol. Rev., 49, 231-252). Examples of such substance abuse include alcohol, cocaine, heroin and nicotine abuse. Other conditions which may be treated by the compounds include substance related disorders, dyskinetic disorders such as Parkinson's disease, neuroleptic-induced parkinsonism and tardive dyskinesias; depression; anxiety, cognitive impairment including memory disorders such as Alzheimers disease, sexual dysfunction, sleep disorders, emesis, amnesia, aggression, vertigo, dementia, circadian rhythm disorders and gastric motility disorders e.g. IBS.

A wide range of psychiatric and neuropsychiatric disorders appear to be related to Obsessive-Compulsive Disorder, and form a family of related disorders referred to as obsessive-compulsive (OC) spectrum disorders. The compounds of the invention may be used for the treatment of an obsessive-compulsive spectrum disorder, including somatoform disorders such as body dysmorphic disorder and hyperchondriasis, bulimia nervosa, anorexia nervosa, binge eating, paraphilia and nonparaphilic sexual addictions, Sydeham's chorea, torticollis, autism, compulsive hoarding, and movement disorders, including Tourette's syndrome. As used herein, the phrase "obsessive-compulsive spectrum disorder" is intended to include Obsessive-Compulsive Disorder.

The compounds of the invention are also useful for the treatment of premature ejaculation.

The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

The term "psychotic disorder" includes:

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The term "substance-related disorder" includes:

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Compounds of the invention may be useful for the treatment of cognition impairment.

The term "cognition impairment" includes cognition impairment in other diseases such as schizophrenia, bipolar disorder, depression, other psychiatric disorders and psychotic conditions associated with cognitive impairment, e.g. Alzheimer's disease.

In a further aspect therefore the present invention provides a method of treating a condition for which modulation of dopamine receptors (especially dopamine $D_3$ receptors) is beneficial, which comprises administering to a mammal (e.g. human) in need thereof an effective amount of a compound of the invention.

Modulation, as used herein, especially refers to inhibition/antagonism (which may also translate into inverse agonism in constitutively active receptor systems).

In one embodiment, the condition is a substance-related disorder, a psychotic disorder, an obsessive compulsive spectrum disorder or premature ejaculation.

The invention also provides a compound of the invention for use in therapy.

The invention also provides a compound of the invention for use in the treatment of a condition in a mammal for which modulation of dopamine receptors (especially dopamine $D_3$ receptors) is beneficial.

The invention also provides the use of a compound of the invention in the manufacture of a medicament for the treatment of a condition in a mammal for which modulation of dopamine receptors (especially dopamine $D_3$ receptors) is beneficial.

In one embodiment, compounds of the invention are used in the treatment of psychoses such as schizophrenia, in the treatment of substance abuse, in the treatment of obsessive compulsive spectrum disorders, in the treatment of premature ejaculation.

Also provided is the use of a compound of the invention in the manufacture of a medicament for the treatment of a psychotic condition, substance abuse in a mammal, obsessive compulsive spectrum disorders, and premature ejaculation.

Also provided is a compound of the invention for use in the treatment of a psychotic condition (e.g. schizophrenia), substance abuse, obsessive compulsive spectrum disorders, and premature ejaculation in a mammal.

Also provided is a compound of the invention or for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of the invention and a pharmaceutically acceptable carrier. The pharmaceutical composition can be for use in the treatment of any of the conditions described herein.

Compound of the invention may be administered by any convenient method, for example by oral, parenteral (e.g. intravenous), buccal, sublingual, nasal, rectal or transdermal administration and the pharmaceutical compositions adapted accordingly.

Compound of the invention which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the invention calculated as the free base.

The compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Functional potency of compounds of this invention can be measured by the following GTPS scintillation proximity assay (GTPS-SPA). Cells used in the study are Chinese Hamster Ovary (CHO) Cells.

Cell Line

CHO_D2
CHO_D3

Dopamine CHO $D_3$ (Biocat no 1060) transduced with bacmam G0 G-protein (Biocat no 97886)

All steps are performed at 4° C. Cell membranes are prepared as follows. Cell pellets are resuspended in 10 volumes of 50 mM HEPES, 1 mM EDTA pH 7.4, using KOH. Cells are homogenised within a glass waring blender for 2 bursts of 15 secs in 200 mls of buffer (50 mM HEPES, 1 mM leupeptin, 25 µg/ml bacitracin, 1 mM EDTA, 1 mM PMSF, 2 µM Pepstatin A). (the latter 2 reagents added as fresh ×100 and ×500 stocks respectively in ethanol). The blender is plunged into ice for 5 mins after the first burst and 10-40 mins after the final burst to allow foam to dissipate. The material is then spun at 500 g for 20 mins and the supernatant spun for 36 mins at 48,000 g. The pellet is resuspended in the same buffer as above but without PMSF and Pepstatin A. The material is then forced through a 0.6 mm needle, made up to the required volume, (usually ×4 the volume of the original cell pellet), aliquoted and stored frozen at −80° C.

The final top concentration of test drug is 3 µM in the assay and 11 points serial dilution curves 1:4 in 100% DMSO are carried out using a Biomek FX. The test drug at 1% (0.5 ul) total assay volume (TAV) is added to a solid, white Greiner polypropylene 384-well assay plate. 50% TAV (250) of pre-coupled (for 60 mins at RT) membranes, 5 µg/well, and Wheatgerm Agglutinin Polystyrene Scintillation Proximity Assay beads (RPNQ0260, Amersham), 0.25 mg/well, in 20 mM HEPES (pH 7.4, 100 mM NaCl, 10 mM MgCl2), 60 µg/mL saponin and 30 uM GDP is added. The third addition is a 20% TAV (10 ul) addition of either buffer, (agonist format) or EC80 final assay concentration of agonist, Quinelorane, prepared in assay buffer (antagonist format). The assay is started by the addition of 29% TAV (15 ul) of GTP[35S] 0.38 nM final (37 MBq/mL, 1160 Ci/mmol, Amersham). After all additions assay plates are spun down for 1 min at 1,000 rpm. The final assay cocktail (45.5 µl) is incubated at room temperature to equilibrate for 3-6 hours before reading on a ViewLux™ (613/55 filter) luminescence imager 5 min/plate.

The effect of the test drug over the basal generates fpKi values of test drug are calculated from the $IC_{50}$ generated by "antagonist format" experiment, using Cheng & Prusoff equation: fKi=IC50/1+([A]/EC50) where: [A] is the concentration of the agonist Quinelorane in the assay and EC50 is the Quinelorane EC50 value obtained in the same experiment. fpKi is defined as −log fKi.

pKi results are only estimated to be accurate to about 0.3-0.5.

In the context of the present invention functional pKi (fpKi, corresponding to the negative logarithm of fKi) is used instead of functional Ki (fKi) and the compounds of formula (I) and salts thereof typically show fpKi for D3 receptors comprised between approximately 7.0 and 8.5.

Here below a list of examples is provided which showed no activity in the D2 GTPS-SPA assay up to the highest concentration tested in the assay (3 µM) and thus considered to be selective for D3 over D2 receptors:
E3, E4, E5, E6, E7, E8, E9, E11, E12.

EXAMPLES

Unless otherwise noted, all starting materials were obtained from commercial suppliers and used without any further purification.

In the procedures that follow, after each starting material, reference to a Preparation or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

Compounds may be named using ACD/Name PRO6.02 chemical naming software (Advanced Chemistry Development Inc., Toronto, Ontario, M5H2L3, Canada) or ISIS/Draw 2.5 SR 2 Autonom (MDL Information System, Inc).

All temperatures refer to ° C. (degrees Centigrade).

Proton Magnetic Resonance (NMR) spectra may be typically recorded either on Varian instruments at 300, 400 or 500 MHz, or on a Bruker instrument at 300 and 400 MHz. Chemical shifts are expressed in parts of million (ppm, δ units). Coupling constants are in units of hertz (Hz) chemical shifts are reported in ppm downfield (d) from $Me_4Si$, used as internal standard, and are assigned as singlets (s), broad singlets (bs), doublets (d), doublets of doublets (dd), triplets (t), quartets (q) or multiplets (m).

Mass spectra (MS) are typically taken on a 4 II triple quadrupole Mass Spectrometer (Micromass UK) or on a Agilent MSD 1100 Mass Spectrometer, operating in ES (+) and ES (−) ionization mode or on an Agilent LC/MSD 1100 Mass Spectrometer, operating in ES (+) and ES (−) ionization mode coupled with HPLC instrument Agilent 1100 Series. In the mass spectra only one peak in the molecular ion cluster is reported.

LCMS may be typically recorded under the following conditions:

DAD chromatographic traces, mass chromatograms and mass spectrums are typically taken on a HPLC/MS Acquity™ system coupled with a Micromass ZQ™ mass spectrometer operating in ESI positive. The phases used are: A) H2O/ACN 95/5+0.1% TFA; B) H2O/ACN 5/95+0.1% TFA. The gradient is: t=0 min) 95% A 5% B, t=0.25) 95% A 5% B, t=3.30) 100% B, t=4.0) 100% B, followed by 1 min of reconditioning Column: Acquity BEH C18 2.1×50 mm 1.7 um 35° C. Flow: 600 uL/min.

Mass tune: Capillary 3.25 kV, cone 20V, source temperature 115° C. desolvation T 350° C.

Preparative LC-MS purifications may be typically performed under the following conditions: Instrument: HPLC-MS preparative system Waters (2767 and 2525) coupled with photodiode array detector and Micromass ZQ. Column: Waters XTerra MS C18 (19×300 mm, 10 um). Flow rate 20 ml/min. Mobile phase: A phase=water+0.1% TFA, B phase=acetonitrile+0.1% TFA. 0-3.0 min (A: 90%, B: 10%), 3.0 min (A: 90%, B: 10%), 3.0-26.0 min (A: 5%, B: 95%), 26.0 min (A: 5%, B: 95%), 26.0-30.0 min (A: 5%, B: 95%), 30.0 min (A: 5%, B: 95%), 30.0-30.5 min (A: 90%, B: 10%), 30.5 min (A: 90%, B: 10%), 30.5-31.5 min (A: 90%, B: 10%). The fractions containing the pure material may be collected and the solvents evaporated. The so obtained trifluoroacetate salts may be neutralized by passing over SCX cartridge.

Preparative HPLC purifications may be typically performed under the following conditions:

Instrument: Shimadzu (LC/8A and SCL/10A) coupled with UV spectrophotometric dector (SPD/6A). Column: Waters SymmetryPrep C18 19×30 mm×7 um; flow rate: 20 ml/min; mobile phase: A phase=water/acetonitrile 9/1+0.5% TFA, B phase=water/acetonitrile 5/95+0.5% TFA using a 30 min gradient of 5-100% solvent B.

The fractions containing the pure material may be collected and the solvents evaporated.

The so obtained trifluoroacetate salts may be neutralized by passing over SCX cartridge.

For reactions involving microwave irradiation, a Personal Chemistry Emrys™ Optimizer may be used.

Flash silica gel chromatography may be carried out on silica gel 230-400 mesh (supplied by Merck AG Darmstadt, Germany) or over Varian Mega Be—Si pre-packed cartridges or over pre-packed Biotage silica cartridges.

In a number of preparations, purification may be performed using either Biotage manual flash chromatography (Flash+) or automatic flash chromatography (Horizon) systems. All these instruments work with Biotage Silica cartridges.

Optical rotations may be measured using a (Perkin Elmer Model 341) polarimeter operating at 589 nm (Sodium source). Measurements may be made using a 1 decimeter microcell thermostated at 23° C. Concentrations may be typically 10 mg/ml (c=1).

Melting point determination may be performed on a Buchi B-540 apparatus.

Column chromathography may be carried out over silica gel (Merck AG Darmstaadt, Germany).

The following abbreviations are used in the text: n-PrOH=n-propanol, Pd(Oac)₂, MeOH=Methanol, DCM=dichloromethane, DMSO=dimethyl sulfoxide; DMF=N,N'-dimethylformamide; THF=tetrahydrofuran, Pd(dba)₂=palladiumdibenzylideneacetone, DIPEA=diisopropylethylemine; DME=dimethoxyethane, TEA=triethylamine; DCE=dichloroethane, Tlc refers to thin layer chromatography on silica plates, and dried refers to a solution dried over anhydrous sodium sulphate, r.t. (RT) refers to room temperature, Rt=retention time, SPE Cartridge=Solid Phase Extraction Cartridge; SCX Cartridge=Strong Cation Exchange Cartridge, PS-isocyanate=polimer supported isocyanate resin.

Preparation 1:
3-[4-(trifluoromethyl)phenyl]-1H-pyrrole-2,5-dione (Prep1)

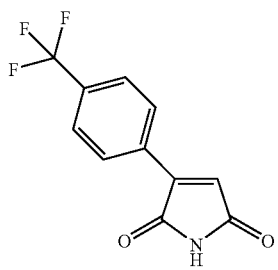

A mixture of hydrochloric acid (37% in water, 285 mL) and water (190 mL) was added to 4-(trifluoromethyl)aniline (150 g, 116 mL) at room temperature with vigorous stirring and the formed precipitate was allowed to stir for further 30 minutes. Temperature was reduced to 0° C. and sodium nitrite (70.6 g) in 180 mL of water was added dropwise to the stirred suspension. At the end of diazotisation, a clear yellow solution was obtained. Maleimide (180 g) in acetone (1.1 L) was added dropwise at 0° C. and then the pH of the solution was adjusted to 3-3.5 by adding sodium acetate. Copper (II) chloride (18.8 g) was added to the vigorously stirred mixture. After a few minutes a gas started to develop (conspicuous foaming). The reaction mixture was allowed to stir at 0° C. for 1 h and overnight at room temperature. Acetone was removed in vacuo, the residue was filtered and dried overnight in vacuo to give the title compound (155 g) as a light brown solid.

MS (m/z): 242.2 [MH]⁺.

Preparation 2: (1R,5S/1S,5R)-1-[4-(trifluoromethyl)phenyl]-3-azabicyclo[3.1.0]-hexane-2,4-dione (Prep2)

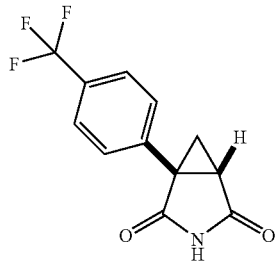

Milled sodium hydroxide (40 g) was added in small portions to a stirred solution of trimethylsulfoxonium iodide (219 g) in DMSO (anhydrous, 2 L). The resulting mixture was allowed to stir at room temperature for 1.5 h. 3-[4-(Trifluoromethyl)phenyl]-1H-pyrrole-2,5-dione (Prep1, 120 g) dissolved in DMSO (anhydrous, 0.5 L) was then added dropwise and the resulting mixture was allowed to stir at room temperature for 20 minutes. Temperature was then reduced to 0° C. and aqueous saturated NH₄Cl (2 L) was slowly added, followed by Et₂O (1 L). After separation of the two phases, the aqueous layer was repeatedly extracted with Et₂O (3×1 L). Combined organic layers were washed with brine (2×1 L) and then dried over Na₂SO₄. Evaporation of the solvent gave a light brown solid which was suspended in 1 L of dichloromethane and 1 L of cyclohexane. The mixture was allowed to stir at room temperature for 45 minutes and then filtered to give the title compound (116 g) as white solid.

MS (m/z): 256.1 [MH]⁺.

Preparation 3: (1R,5S/1S,5R)-1-[4-(trifluoromethyl)phenyl]-3-azabicyclo[3.1.0]-hexane (Prep3)

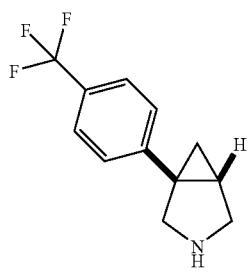

Borane (1M in tetrahydrofuran, 1.4 l) was charged into a 5 l reactor under N₂ and cooled at 0° C. (1R,5S/1S,5R)-1-[4-(trifluoromethyl)phenyl]-3-azabicyclo[3.1.0]hexane-2,4-dione (Prep2, 101 g) dissolved in anhydrous THF (1 L) was then added dropwise with vigorous stirring whereby the temperature was constantly kept below 5° C. and gas evolution was monitored. At the end of the addition the resulting mixture was allowed to stir at 0° C. for 1 h and then at room temperature overnight. The mixture was then cooled to 0° C. and methanol (200 mL) followed aqueous 6M hydrochloric acid solution (0.8 L) were cautiously added monitoring gas evolution. THF was then removed in vacuo, the residue was cooled to 0° C. and an aqueous 5M sodium hydroxide solution was added until pH 9-10 had been reached. The aqueous layer was extracted with Et₂O (3×1 L). Removal of solvent in vacuo gave the title compound (140 g) as colorless oil.

MS (m/z): 228.1 [MH]⁺.

Preparation 4: (1S,5R)-1-[4-(trifluoromethyl)phenyl]-3-azabicyclo[3.1.0]hexane (Prep4)

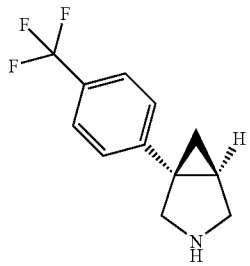

(S)-(+)-Mandelic acid (94 g) was added in portions to a stirred solution of (1R,5S/1S,5R)-1-[4-(trifluoromethyl)phenyl]-3-azabicyclo[3.1.0]hexane (Prep3, 140 g) in 1.4 L of THF. The resulting mixture was stirred at room temperature for 2 h until a white precipitate was formed. The mixture was then warmed up to reflux temperature, stirred for 45 minutes and then slowly cooled down to room temperature. The white solid was collected by filtration and dried in vacuo. This material was recrystallised 4 times from THF (10 volumes) to give 32.5 g of a white solid. This material was then suspended in sodium hydroxide (1M solution, 400 mL) and Et₂O (400 mL) and allowed to stir at room temperature until complete dissolution. After separation of the two phases, the aqueous layer was extracted again with Et₂O (3×250 mL). Combined organic layers were washed with aqueous 1M sodium hydroxide solution (3×200 mL) and then dried over Na₂SO₄. Evaporation of solvent in vacuo gave the title compound (19 g) as white solid. The absolute configuration of the optical isomers was assigned as described in PCT International Publication WO2005/080382.

NMR (¹H, CDCl₃): δ 7.51 (d, 2H), 7.25 (d, 2H), 3.20 (d, 1H), 3.0-3.1 (m, 3H), 1.69 (m, 1H), 0.8-1.0 (m, 2H), NH not observed. MS (m/z): 228.1 [MH]⁺.

Analytical Chromatography

Column: chiralcel OD 10 um, 250×4.6 mm

Mobile phase: A: n-Hexane; B: Isopropanol+0.1% Isopropyl amine

Gradient: isocratic 2% B

Flow rate: 1 mL/min

UV wavelength range: 200-400 nm

Analysis time 25 min

| ret. time (min) | % a/a | |
|---|---|---|
| 16.5 | 0.4 | (1R,5S)-1-[4-(trifluoromethyl)phenyl]-3-azabicyclo[3.1.0]hexane |
| 21.7 | 99.6 | title compound |

Specific Optical Rotation: [α]_D=−10° (CDCl₃, T=20° C., c≈0.004 g/0.8 mL).

Preparation 5: 1-(4-chlorobutyl)-4-phenyl-2(1H)-pyrimidinone (Prep5)

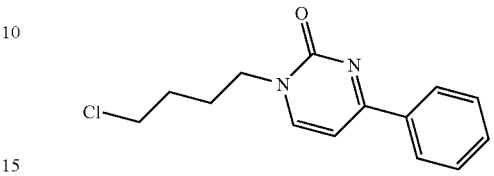

The title compound was prepared using a similar procedure as set out in PCT Publication WO2004/080981.

MS (m/z): 207 [MH]+.

Preparation 6: 1-(4-chlorobutyl)-4-methyl-2(1H)-pyrimidinone (Prep6)

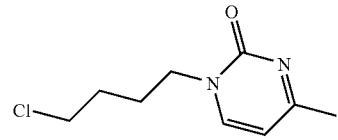

The title compound was prepared using a similar procedure as set out in the PCT Publication WO2004/080981.

MS (m/z): 201 [MH]+.

Preparation 7:
5-Methyl-2-methylsulfanyl-3H-pyrimidin-4-one (Prep7)

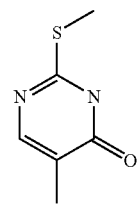

A solution of 85% KOH (3.3 g, 50.7 mmol) and 5-methyl-2-thioxo-2,3-dihydro-1H-pyrimidin-4-one (7.2 g, 50.7 mmol) in absolute EtOH (100 ml) was stirred for 1 hour and then MeI (7.2 g, 50.7 mmol) was added dropwise. After refluxing the mixture for 2 hours, the solvent was removed under vacuum. The residue was triturated with water and the solid was filtered and dried in an oven to give 6.86 g of the title compound as a white powder (87% yield)

MS (ES) m/z 157.1 [M+H]⁺. .

Preparation 8: 4-Chloro-5-methyl-2-methylsulfanyl-pyrimidine (Prep8)

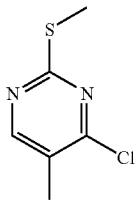

A mixture of 5-methyl-2-methylsulfanyl-3H-pyrimidin-4-one (6.86 g, 44 mmol) and POCl$_3$ (14 ml) in dioxane (60 ml) was refluxed for 2 hours. The solvent was removed under vacuum and the residue was quenched with ice and extracted with diethylether. The organic phase was dried (Na$_2$SO$_4$) and evaporated to give 6.8 g of the title compound as oil that was used in the next step without further purification. (89% yield)

MS (ES) m/z 175.1 [M+H]$^+$.

Preparation 9: 5-Methyl-2-methylsulfanyl-4-pyridin-3-yl-pyrimidine (Prep 9)

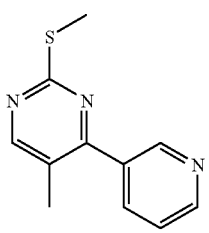

A mixture of 4-chloro-5-methyl-2-methylsulfanyl-pyrimidine (1.24 g, 7.1 mmol), pyridine-3-boronic acid (1.04 g, 8.46 mmol), Na$_2$CO$_3$ (863 mg, 7.76 mmol), PPh$_3$ (186 mg, 0.71 mmol) and Pd(OAc)$_2$ (40 mg) in n-PrOH (50 ml) was refluxed for 2 hours. The solvent was then evaporated under vacuum and the crude was partitioned between water and ethyl acetate. The organic phase was dried (Na$_2$SO$_4$) and evaporated. The crude was purified by flash chromatography with ethyl acetate-petroleum ether (1-1) to afford 1.28 g of the title compound as a white solid (83% yield)

MS (ES) m/z 218.2 [M+H]$^+$.

Preparation 10: 2-Methanesulfonyl-5-methyl-4-pyridin-3-yl-pyrimidine (Prep10)

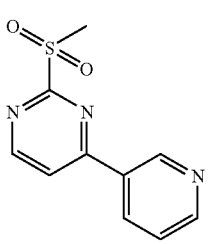

A solution of 5-methyl-2-methylsulfanyl-4-pyridin-3-yl-pyrimidine (1.28 g, 5.90 mmol) in MeOH (45 ml) was cooled at 0° C. and then an aqueous solution of oxone (11 g, 17.95 mmol in 45 ml of water) was added dropwise. After 15 minutes, ice bath was removed and the stirring continue for 3 hours. The mixture was neutralized with solid NaHCO$_3$ and the product was extracted with ethyl acetate. The organic phase was dried (Na$_2$SO$_4$) and evaporated to give 1.3 g of the title compound as a white powder (88% yield).

MS (ES) m/z 250 [M+H]$^+$.

Preparation 11: 5-Methyl-4-pyridin-3-yl-1H-pyrimidin-2-one (Prep11)

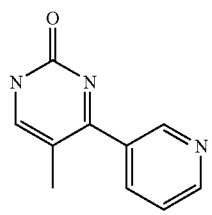

2-Methanesulfonyl-5-methyl-4-pyridin-3-yl-pyrimidine (1.3 g, 5.22 mmol) was dissolved in dioxane (80 ml) and then 2N NaOH$_{aq}$ (21 ml, 42 mmol) was added dropwise at room temperature. After stirring for 1 hour, the solution was neutralized with 37% HCl$_{aq}$. The residue was purified by flash chromatography with DCM-MeOH—NH$_4$OH (9-1-0.1) to give 951 mg of the title compound as a light brown powder. (97% yield).

MS (ES) m/z 188.2 [M+H]$^+$.

Preparation 12: 1-(4-Chloro-butyl)-5-methyl-4-pyridin-3-yl-1H-pyrimidin-2-one (Prep12)

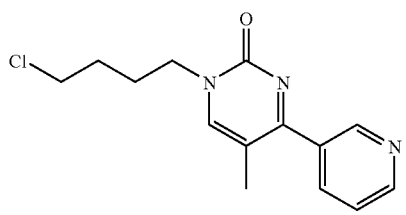

To a solution of 5-methyl-4-pyridin-3-yl-1H-pyrimidin-2-one (100 mg, 0.53 mmol) in DMSO (2 ml), 60% NaH (23 mg, 0.59 mmol) was added portionwise. After heating the mixture at 60° C. for 1 hour, 1-bromo-4-chloro-butane (100 mg, 0.59 mmol) dissolved in DMSO (0.8 ml) was added at 60° C. and the heating was maintained for further 2 hours. After cooling to room temperature, water was added and the mixture extracted with diethyl ether to remove the dialkylated product and finally with ethyl acetate. Ethyl acetate was washed with brine, dried (Na$_2$SO$_4$) and evaporated to afford 100 mg of the title compound as yellow oil (68% yield).

MS (ES) m/z 278 [M+H]$^+$.

Preparation 13: 4-Iodo-2-methylsulfanyl-pyrimidine (Prep 13)

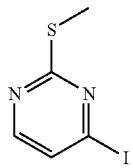

4-Chloro-2-methylsulfanyl-pyrimidine (2 ml, 17 mmol) and 57% HI$_{aq}$ (15.46 ml) were mixed and stirred at room temperature for 2 days. The mixture was extracted with DCM and washed with a solution of NaS$_2$O$_3$ and then with 5% NaHCO$_3$. The organic phase was dried (Na$_2$SO$_4$) and evaporated to give 3.4 g of the title compound that was used in the next step without further purification. (80% yield)

MS (ES) m/z 253.1 [M+H]$^+$.

Preparation 14: 4-(6-Methyl-pyridin-2-yl)-2-methylsulfanyl-pyrimidine (Prep 14)

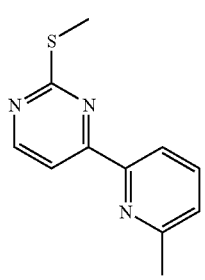

4-Iodo-2-methylsulfanyl-pyrimidine (1 g, 3.97 mmol) was dissolved in dry and degassed THF (9 ml). Pd(dba)$_2$ (114 mg, 0.20 mmol) and tri(2-furyl)phosphine (50 mg, 0.20 mmol) were added. The mixture was cooled at 0° C. and then a 0.5 M solution of 6-methyl-2-pyridylzinc bromide in THF (13 ml, 6.5 mmol) was slowly added dropwise. After stirring the mixture at room temperature for 3 hours, ethyl acetate was added and the mixture was washed with water. The organic phase was dried (Na$_2$SO$_4$) and evaporated. The residue was purified by flash chromatography DCM-MeOH—NH$_4$OH (20-0.1-0.1) to give 785 mg of the title compound (90% yield).

MS (ES) m/z 218 [M+H]$^+$.

Preparation 15: 2-Methanesulfonyl-4-(6-methyl-pyridin-2-yl)-pyrimidine (Prep15)

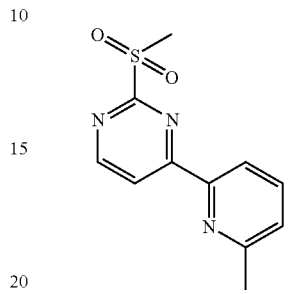

A solution of 4-(6-methyl-pyridin-2-yl)-2-methylsulfanyl-pyrimidine (785 mg, 3.61 mmol) in MeOH (25 ml) was cooled at 0° C. and then an aqueous solution of oxone (6.67 g, 10.85 mmol in 25 ml of water) was slowly added. After stirring 3 hours at room temperature, the mixture was basified with 5% NaHCO$_3$ and the product was extracted with ethyl acetate. The organic phase was dried (Na$_2$SO$_4$) and evaporated to give 625 mg of the title compound that was used in the next step without further purification (70% yield).

MS (ES) m/z 250 [M+H]$^+$.

Preparation 16: 4-(6-Methyl-pyridin-2-yl)-1H-pyrimidin-2-one (Prep16)

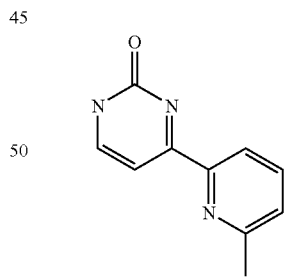

2-Methanesulfonyl-4-(6-methyl-pyridin-2-yl)-pyrimidine (625 mg, 2.51 mmol) was dissolved in dioxane (20 ml) and then 2N NaOH$_{aq}$ (12.5 ml, 25 mmol) was added. After stirring at room temperature for 1 hour, the solution was acidified with 37% HCl$_{aq}$. The mixture was evaporated and the residue redissolved in DCM-MeOH—NH$_4$OH (95-5-0.5) and evaporated. The crude was purified by Flash chromatography with DCM-MeOH (9-1) to give 400 mg of the title compound. (85% yield).

MS (ES) m/z 188.2 [M+H]$^+$.

Preparation 17: 1-(4-Chloro-butyl)-4-(6-methyl-pyridin-2-yl)-1H-pyrimidin-2-one (Prep17)

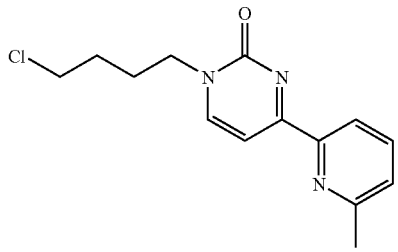

To a solution of 4-(6-methyl-pyridin-2-yl)-1H-pyrimidin-2-one (200 mg, 1.06 mmol) in dry DMF (20 ml), 60% NaH (55 mg, 1.39 mmol) was added portionwise. After heating the mixture at 100° C. for 1 hour, 1-bromo-4-chloro-butane (187 μl 1.39 mmol) was added and the mixture was stirred overnight at room temperature. Water was added and the mixture extracted with diethyl ether to remove the dialkylated product and finally with ethyl acetate. Ethyl acetate was washed with brine, dried ($Na_2SO_4$) and evaporated. The residue was triturated with petroleum ether to give 173 mg of the title compound as a solid (58% yield).

MS (ES) m/z 278 $[M+H]^+$.

Preparation 18: 4-Iodo-2-methylsulfanyl-pyrimidine (Prep 18)

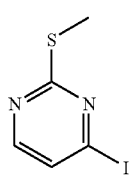

4-Chloro-2-methylsulfanyl-pyrimidine (1 ml, 8.5 mmol) and 57% $HI_{aq}$ (7.73 ml) were mixed and stirred at room temperature for 4 days. The mixture was extracted with DCM and washed with a solution of $NaS_2O_3$ and then with 5% $NaHCO_3$. The organic phase was dried ($Na_2SO_4$) and evaporated, the residue was triturated with petroleum ether to give 1.57 g of the title compound that was used in the next step without further purification. (72% yield)

MS (ES) m/z 253.1 $[M+H]^+$.

Preparation 19: 4-(2,2-Difluoro-benzo[1,3]dioxol-4-yl)-2-methylsulfanyl-pyrimidine (Prep19)

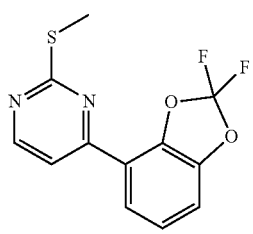

4-Iodo-2-methylsulfanyl-pyrimidine (453 mg, 1.79 mmol), 2,2-difluoro-benzo[1,3]dioxole-4-boronic acid (727 mg, 3.59 mmol), $Na_2CO_3$ (380 mg, 3.59 mmol), 2-(dicyclohexylphosphino)biphenyl (125 mg, 0.36 mmol) were suspended in degassed DME-water solution (5-1, 6.5 ml). After bubbling $N_2$ into the mixture for 20 minutes, $Pd(PPh_3)_4$ (413 mg, 0.36 mmol) was added and the mixture was stirred at 90° C. for 3 hours. The solvent was evaporated under vacuum and the crude was dissolved in DCM and washed with water and brine. The organic phase was dried ($Na_2SO_4$) and evaporated; the crude was purified by flash chromatography with hexane-ethyl acetate (8-2) to give the title compound (326 mg, 65% yield).

MS (ES) m/z 283.2 $[M+H]^+$.

Preparation 20: 4-(2,2-Difluoro-benzo[1,3]dioxol-4-yl)-2-methanesulfonyl-pyrimidine (Prep20)

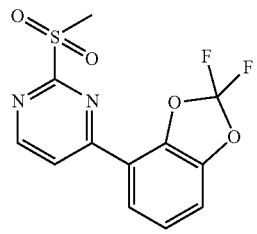

A solution of 4-(2,2-difluoro-benzo[1,3]dioxol-4-yl)-2-methylsulfanyl-pyrimidine (326 mg, 1.15 mmol) in MeOH (8 ml) was cooled at 0° C. and then an aqueous solution of oxone (2.31 g, 3.76 mmol in 8 ml of water) was slowly added. After stirring 2 hours at room temperature, the mixture was basified with 5% $NaHCO_3$ and the product was extracted with ethyl acetate. The organic phase was dried ($Na_2SO_4$) and evaporated to give 364 mg of the title compound that was used in the next step without further purification (quantitative yield).

MS (ES) m/z 315 $[M+H]^+$.

Preparation 21: 4-(2,2-Difluoro-benzo[1,3]dioxol-4-yl)-1H-pyrimidin-2-one (Prep 21)

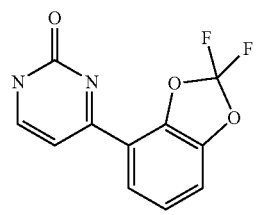

4-(2,2-difluoro-benzo[1,3]dioxol-4-yl)-2-methanesulfonyl-pyrimidine (364 mg, 1.15 mmol) was dissolved in dioxane (8.5 ml) and then 2N $NaOH_{aq}$ (5.7 ml, 11 mmol) was added. After stirring at room temperature for 1 hour, the solution was acidified with 37% $HCl_{aq}$. The mixture was evaporated and the residue was purified by flash chromatography with DCM-MeOH (9-1) to give 232 mg of the title compound. (quantitative yield)

MS (ES) m/z 253 $[M+H]^+$..

Preparation 22: 1-(4-Chloro-butyl)-4-(2,2-difluoro-benzo[1,3]dioxol-4-yl)-1H-pyrimidin-2-one (Prep22)

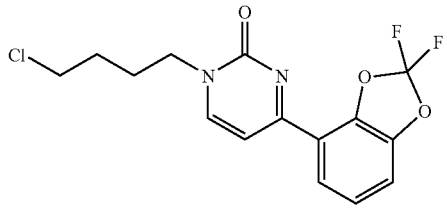

To a solution of 4-(2,2-difluoro-benzo[1,3]dioxol-4-yl)-1H-pyrimidin-2-one (232 mg, 0.92 mmol) in dry DMF (18 ml), 60% NaH (47 mg, 1.19 mmol) was added portionwise under inert atmosphere. After heating the mixture at 100° C. for 1 hour, 1-bromo-4-chloro-butane (137 μl 1.19 mmol) was added and the mixture was stirred overnight at room temperature. Water was added and the mixture extracted with diethyl ether. The organic layer was dried (Na$_2$SO$_4$) and evaporated. The residue purified by flash chromatography with hexane-ethyl acetate (8-2) to give 123 mg of the title compound (39% yield).

MS (ES) m/z 343 [M+H]$^+$.

Preparation 23: 4-Iodo-2-methylsulfanyl-pyrimidine (Prep23)

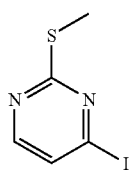

4-Chloro-2-methylsulfanyl-pyrimidine (1.04 ml, 9.0 mmol) and 57% HI$_{aq}$ (10.56 ml) were mixed and stirred at room temperature for 18 hours. The mixture was extracted with DCM and washed with a solution of NaS$_2$O$_3$ and then with 5% NaHCO$_3$. The organic phase was dried (Na$_2$SO$_4$) and evaporated; the residue was triturated with petroleum ether to give 1.82 g of the title compound as a yellow solid (79% yield).

MS (ES) m/z 253.1 [M+H]$^+$.

Preparation 24: 4-(2-Methyl-pyridin-3-yl)-2-methyl-sulfanyl-pyrimidine (Prep24)

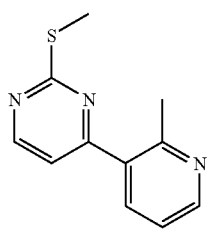

To a solution of 4-iodo-2-methylsulfanyl-pyrimidine (600 mg, 2.38 mmol), 2-methylpyridine-3-boronic acid (533 mg, 3.09 mmol), Na$_2$CO$_3$ (756 mg, 7.14 mmol), triphenylphosphine (62 mg, 0.24 mmol) in nPrOH (10 ml), Pd(OAc)$_2$ (16 mg, 0.07 mmol) was added and the mixture was stirred at 96° C. for 1.5 hours. The solvent was evaporated under vacuum, and the crude was dissolved in DCM and washed with water. The organic phase was dried (Na$_2$SO$_4$) and evaporated. A second batch of this compound was prepared according to the same protocol starting from 0.45 mmol of 4-iodo-2-methylsulfanyl-pyrimidine. The residues, deriving from the two batches, were purified by flash chromatography with DCM-MeOH—NH$_4$OH (20-0.1-0.2) to give 568 mg of the title compound (92% yield).

MS (ES) m/z 218 [M+H]$^+$.

Preparation 25: 2-Methanesulfonyl-4-(2-methyl-pyridin-3-yl)-pyrimidine (Prep25)

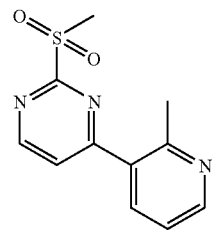

A solution of 4-(2-methyl-pyridin-3-yl)-2-methylsulfanyl-pyrimidine (530 mg, 2.44 mmol) in MeOH (18 ml) was cooled at 0° C. and then an aqueous solution of oxone (4.51 g, 7.32 mmol in 18 ml of water) was slowly added. After stirring 1.5 hours at room temperature, the mixture was basified with 5% NaHCO$_3$ and the product was extracted with ethyl acetate. The organic phase was dried (Na$_2$SO$_4$) and evaporated to give 500 mg of the title compound that was used in the next step without further purification (80% yield).

MS (ES) m/z 250 [M+1-1]$^+$.

Preparation 26: 4-(2-Methyl-pyridin-3-yl)-1H-pyrimidin-2-one (Prep 26)

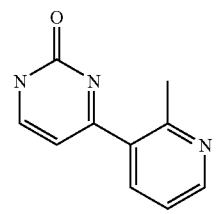

2-Methanesulfonyl-4-(2-methyl-pyridin-3-yl)-pyrimidine (446 mg, 1.79 mmol) was dissolved in dioxane (13 ml) and then 2N NaOH$_{aq}$ (8.9 ml, 17.9 mmol) was added. After stirring at room temperature for 1 hour, the solution was acidified with 37% HCl$_{aq}$. The mixture was evaporated and the residue was re-dissolved in DCM-MeOH—NH$_4$OH (95-5-0.5) and evaporated. The crude was purified by flash chromatography with DCM-MeOH (9-1) to give 343 mg of the title compound. (quantitative yield)

MS (ES) m/z 188.2 [M+H]$^+$..

Preparation 27: 1-(4-Chloro-butyl)-4-(2-methyl-pyridin-3-yl)-1H-pyrimidin-2-one (Prep27)

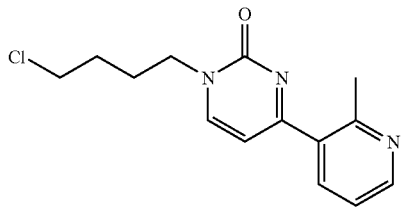

To a solution of 4-(2-methyl-pyridin-3-yl)-1H-pyrimidin-2-one (199 mg, 1.06 mmol) in dry DMF (20 ml), 60% NaH (55 mg, 1.38 mmol) was added portionwise under inert atmosphere. After heating the mixture at 100° C. for 1 hour, 1-bromo-4-chloro-butane (160 µl, 1.38 mmol) was added and the mixture was stirred at room temperature for 1 hour and heated at 70° C. for 2 hours. Water was added and the mixture extracted with diethyl ether and with ethyl acetate. The organic layers were mixed together, dried (Na$_2$SO$_4$) and evaporated to afford 161 mg of the title compound that was used in the next step without further purification (54% yield).

MS (ES) m/z 278 [M+H]$^+$.

Preparation 28: 4-(2-Methyl-pyridin-4-yl)-2-methyl-sulfanyl-pyrimidine (Prep28)

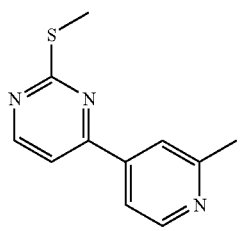

To a solution of 4-chloro-2-methylsulfanyl-pyrimidine (781 mg, 4.86 mmol) in degassed nPrOH (55 ml), 2-methylpyridine-4-boronic acid (800 mg, 5.84 mmol), Na$_2$CO$_3$ (619 mg, 5.47 mmol), triphenylphosphine (127 mg, 0.486 mmol) and Pd(OAc)$_2$ (32 mg, 0.15 mmol) were added. The mixture was stirred at 100° C. for 1 hour. The solvent was evaporated under vacuum, and the crude was dissolved in DCM and washed with water. The organic phase was dried (Na$_2$SO$_4$) and evaporated. The crude was purified by flash chromatography with DCM-MeOH—NH$_4$OH (20-0.1-0.2) to give 990 mg of the title compound (93% yield).

MS (ES) m/z 218 [M+H]$^+$.

Preparation 29: 2-Methanesulfonyl-4-(2-methyl-pyridin-4-yl)-pyrimidine (Prep29)

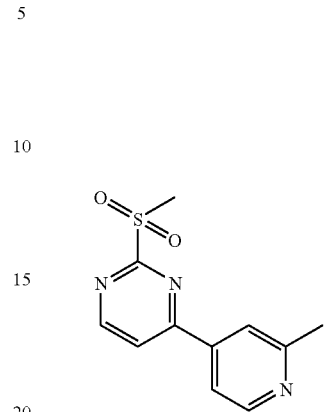

A solution of 4-(2-methyl-pyridin-4-yl)-2-methylsulfanyl-pyrimidine (990 mg, 4.56 mmol) in MeOH (35 ml) was cooled at 0° C. and then an aqueous solution of oxone (8.41 g, 13.85 mmol in 35 ml of water) was slowly added. After stirring 3.5 hours at room temperature, the mixture was basified with solid NaHCO$_3$ and the product was extracted with ethyl acetate. The organic phase was dried (Na$_2$SO$_4$) and evaporated to give 720 mg of the title compound that was used in the next step without further purification (65% yield).

MS (ES) m/z 250 [M+H]$^+$.

Preparation 30: 4-(2-Methyl-pyridin-4-yl)-1H-pyrimidin-2-one (Prep30)

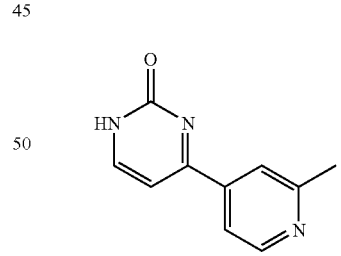

2-Methanesulfonyl-4-(2-methyl-pyridin-4-yl)-pyrimidine (720 mg, 2.89 mmol) was dissolved in dioxane (25 ml) and then 2N NaOH$_{aq}$ (14.4 ml, 28.9 mmol) was added. After stirring at room temperature for 2 hours, the solution was acidified with 37% HCl$_{aq}$. The mixture was evaporated and the residue was re-dissolved in DCM-MeOH—NH$_4$OH (90-10-1) and evaporated. The crude was purified by flash chromatography with DCM-MeOH (9-1) to give 279 mg of the title compound. (52% yield).

MS (ES) m/z 188.2 [M+H]$^+$.

Preparation 31: 1-(4-Chloro-butyl)-4-(2-methyl-pyridin-4-yl)-1H-pyrimidin-2-one (Prep31)

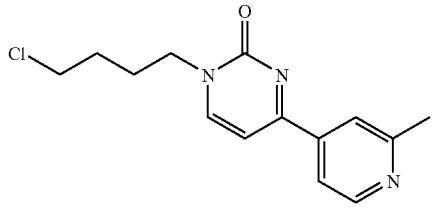

To a solution of 4-(2-methyl-pyridin-4-yl)-1H-pyrimidin-2-one (256 mg, 1.37 mmol) in dry DMF (45 ml), 60% NaH (71 mg, 1.78 mmol) was added portionwise under inert atmosphere. After heating the mixture at 100° C. for 1 hour, 1-bromo-4-chloro-butane (305 mg, 1.78 mmol) was added and the mixture was stirred at room temperature for 1.5 hours and heated at 60° C. for 2 hours. Water was added and the mixture extracted with diethyl ether and with ethyl acetate. The organic layers were mixed together, dried ($Na_2SO_4$) and evaporated to afford 100 mg of the title compound that was used in the next step without further purification in the next step (27% yield).

MS (ES) m/z 278 [M+H]$^+$.

Preparation 32: 4-Iodo-2-methylsulfanyl-pyrimidine (Prep32)

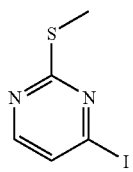

4-Chloro-2-methylsulfanyl-pyrimidine (1.04 ml, 9.0 mmol) and 57% HI$_{aq}$ (10.56 ml) were mixed and stirred at room temperature for 48 hours. The mixture was extracted with DCM and washed with a solution of $NaS_2O_3$ and then with 5% $NaHCO_3$. The organic phase was dried ($Na_2SO_4$) and evaporated; the residue was triturated with petroleum ether to give 1.82 g of the title compound as a yellow solid (79% yield).

MS (ES) m/z 253.1 [M+H]$^+$.

Preparation 33: 4-(3,5-Dimethyl-isoxazol-4-yl)-2-methylsulfanyl-pyrimidine (Prep33)

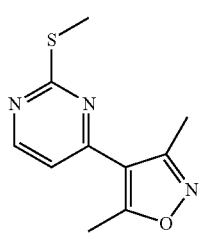

To a solution of 4-iodo-2-methylsulfanyl-pyrimidine (745 mg, 2.95 mmol) in degassed nPrOH (55 ml), 3,5-dimethyl-isoxazole-4-boronic acid (500 mg, 3.54 mmol), $Na_2CO_3$ (375 mg, 3.54 mmol), triphenylphosphine (80 mg, 0.29 mmol) and Pd(OAc)$_2$ (20 mg, 0.09 mmol) were added. The mixture was stirred at 100° C. for 4.5 hours. The solvent was evaporated under vacuum, and the crude was dissolved in DCM and washed with water. The organic phase was dried ($Na_2SO_4$) and evaporated. The crude was purified by flash chromatography with petroleum ether-ethyl acetate (95-5 to 9-1) to give 638 mg of the title compound (97% yield).

MS (ES) m/z 222.2 [M+H]$^+$.

Preparation 34: 4-(3,5-Dimethyl-isoxazol-4-yl)-2-methanesulfonyl-pyrimidine (Prep34)

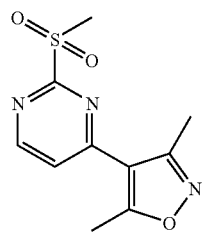

A solution of 4-(3,5-dimethyl-isoxazol-4-yl)-2-methylsulfanyl-pyrimidine (638 mg, 2.88 mmol) in MeOH (23 ml) was cooled at 0° C. and then an aqueous solution of oxone (5.31 g, 8.64 mmol in 23 ml of water) was slowly added. After stirring 1.5 hours at room temperature, the mixture was basified with solid $NaHCO_3$ and the product was extracted with ethyl acetate. The organic phase was dried ($Na_2SO_4$) and evaporated to give 666 mg of the title compound that was used in the next step without further purification (91% yield).

MS (ES) m/z 254 [M+H]$^+$.

Preparation 35: 4-(3,5-Dimethyl-isoxazol-4-yl)-1H-pyrimidin-2-one (Prep35)

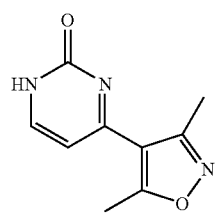

4-(3,5-dimethyl-isoxazol-4-yl)-2-methanesulfonyl-pyrimidine (666 mg, 2.63 mmol) was dissolved in dioxane (20 ml) and then 2N NaOH$_{aq}$ (13.2 ml, 26.3 mmol) was added. After stirring at room temperature for 30 minutes, the solution was acidified with 37% HCl$_{aq}$. The mixture was evaporated and the residue was purified by flash chromatography with DCM-MeOH (9-1) to give the title compound. (quantitative yield).

MS (ES) m/z 192.2 [M+H]$^+$.

Preparation 36: 1-(4-Chloro-butyl)-4-(3,5-dimethyl-isoxazol-4-yl)-1H-pyrimidin-2-one (Prep36)

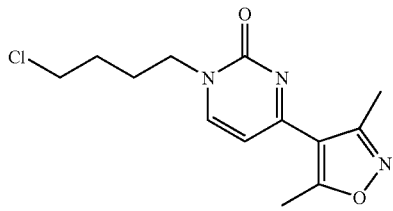

To a solution of 4-(3,5-dimethyl-isoxazol-4-yl)-1H-pyrimidin-2-one (156 mg, 0.82 mmol) in dry DMF (20 ml), 60% NaH (40 mg, 1.06 mmol) was added portionwise under inert atmosphere. After heating the mixture at 100° C. for 1 hour, 1-bromo-4-chloro-butane (123 μl, 1.06 mmol) was added at room temperature and the mixture was heated at 100° C. for 2 hours. Water was added and the mixture extracted with diethyl ether to remove the dialkylated product and finally with ethyl acetate. Ethyl acetate phase was dried (Na$_2$SO$_4$) and evaporated to afford 81 mg of the title compound that was used in the next step without further purification (35% yield).
MS (ES) m/z 282 [M+H]$^+$.

Preparation 37: 4-(2-Fluoro-phenyl)-2-methylsulfanyl-pyrimidine (Prep37)

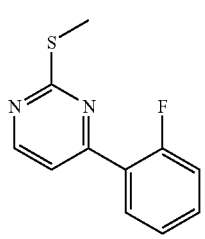

To a solution of 4-chloro-2-methylsulfanyl-pyrimidine (1.00 g, 6.22 mmol), 2-fluoro-phenyl-boronic acid (1.04 g, 6.84 mmol), Na$_2$CO$_3$ (790 mg, 7.45 mmol), triphenylphosphine (163 mg, 0.62 mmol) in nPrOH (50 ml), Pd(OAc)$_2$ (42 mg, 0.187 mmol) was added and the mixture was refluxed for 3 hours. The solvent was evaporated under vacuum, and the crude was dissolved in ethyl acetate and washed with water. The organic phase was dried (Na$_2$SO$_4$) and evaporated; the crude was purified by flash chromatography with petroleum ether-ethyl acetate (97-3 to 95-5) to give the title compound (1.23 g, 90% yield).
MS (ES) m/z 221 [M+H]$^+$

Preparation 38: 4-(2-Fluoro-phenyl)-1H-pyrimidin-2-one (Prep38)

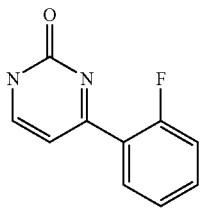

A solution of 4-(2-fluoro-phenyl)-2-methylsulfanyl-pyrimidine (943 mg, 4.28 mmol) in 37% HCl (18 ml) was heated at 100° C. for 21 hours. The mixture was diluted with water then basified with solid NaHCO$_3$. The suspension was extracted with DCM; the organic layer was dried (Na$_2$SO$_4$), filtered and evaporated to give the title compound that was used without further purification in the next step (725 mg, 89% yield)
MS (ES) m/z 191 [M+H]+.

Preparation 39: 1-[4-(tert-Butyl-dimethyl-silanyloxy)-butyl]-4-(2-fluoro-phenyl)-1H-pyrimidin-2-one (Prep39)

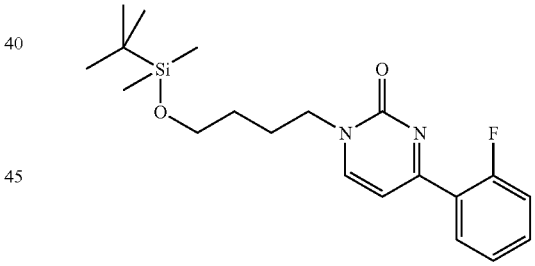

To a solution of 4-(2-fluoro-phenyl)-1H-pyrimidin-2-one (375 mg, 1.97 mmol) in dry DMF (50 ml), 60% NaH (103 mg, 2.56 mmol) was added portionwise. After heating the mixture at 100° C. for 1 hour, tert-butyl-(4-iodo-butoxy)-dimethyl-silane (664 μl 2.56 mmol) was added at room temperature and the mixture was stirred overnight. Water was added and the mixture extracted with diethyl ether; the organic layer was dried (Na$_2$SO$_4$), filtered and evaporated. The residue was purified by flash chromatography with petroleum ether-ethyl acetate (1-1) to give 370 mg of the title compound as a yellow solid (50% yield).
MS (ES) m/z 377 [M+H]$^+$.

Preparation 40: 4-(2-Fluoro-phenyl)-1-(4-hydroxy-butyl)-1H-pyrimidin-2-one (Prep40)

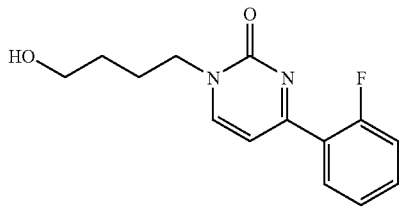

1-[4-(tert-Butyl-dimethyl-silanyloxy)-butyl]-4-(2-fluoro-phenyl)-1H-pyrimidin-2-one (370 mg, 0.98 mmol) was dissolved in 4N HCl in dioxane (15 ml). The mixture was stirred at room temperature for 15 minutes, then basified with 30% $NH_4OH_{aq}$ and finally extracted with DCM. The organic layer was dried ($Na_2SO_4$), filtered and evaporated, to give 258 mg of the title compound as a yellow solid (95% yield).

MS (ES) m/z 263 [M+H]$^+$.

Preparation 41: 4-[4-(2-Fluoro-phenyl)-2-oxo-2H-pyrimidin-1-yl]-butyraldehyde (Prep41)

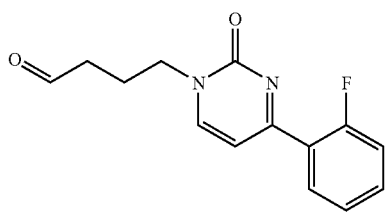

To a solution of 4-(2-fluoro-phenyl)-1-(4-hydroxy-butyl)-1H-pyrimidin-2-one (80 mg, 0.30 mmol) in DCM (8 ml), the solution at 0° C., solid Dess Martin periodinane (380 mg, 0.61 mmol) was added portionwise. The mixture was stirred at room temperature for 1 hour. $Na_2S_2O_3$ was added and the mixture was extracted with DCM; the organic layer was dried ($Na_2SO_4$), filtered and evaporated. The crude was purified by flash chromatography with ethyl acetate to give 50 mg of the title compound as a green solid (64% yield).

MS (ES) m/z 261 [M+H]$^+$.

Preparation 42: 2-Methylsulfanyl-4-pyridin-3-yl-pyrimidine (Prep42)

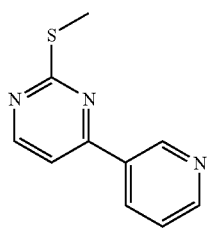

To a solution of 4-chloro-2-methylsulfanyl-pyrimidine (1.00 g, 6.22 mmol), 3-pyridine-boronic acid (918 mg, 7.47 mmol), $Na_2CO_3$ (791 mg, 7.47 mmol), triphenylphosphine (162 mg, 0.62 mmol) in nPrOH (60 ml), Pd(OAc)$_2$ (41 mg, 0.19 mmol) was added and the mixture was stirred at 100° C. for 1 hour. The solvent was evaporated under vacuum, and the crude was dissolved in DCM and washed with water. The organic phase was dried ($Na_2SO_4$) and evaporated; the crude was purified by flash chromatography with DCM-MeOH—$NH_4OH$ (25-0.1-0.1 to 20-0.2-0.2) to give the title compound (1.18 g, 93% yield).

MS (ES) m/z 204.2 [M+H]$^+$.

Preparation 43: 2-Methanesulfonyl-4-pyridin-3-yl-pyrimidine (Prep43)

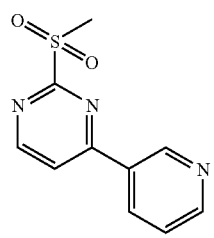

A solution of 2-methylsulfanyl-4-pyridin-3-yl-pyrimidine (1.18 g, 5.81 mmol) in MeOH (45 ml) was cooled at 0° C., then an aqueous solution of oxone (10.7 g, 17.45 mmol in 45 ml of water) was slowly added. After stirring 1.5 hours at room temperature, the mixture was basified with 5% $NaHCO_3$ and the product was extracted with ethyl acetate. The organic phase was dried ($Na_2SO_4$) and evaporated to give 846 mg of the title compound that was used in the next step without further purification (61% yield).

MS (ES) m/z 236 [M+H]$^+$.

Preparation 44: 4-Pyridin-3-yl-1H-pyrimidin-2-one (Prep44)

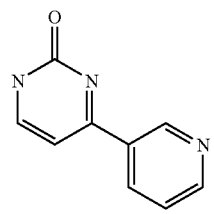

2-Methanesulfonyl-4-pyridin-3-yl-pyrimidine (846 mg, 3.58 mmol) was dissolved in dioxane (36 ml) and then 2N $NaOH_{aq}$ (18 ml, 36 mmol) was added. After stirring at room temperature for 1 hour, the solution was acidified with 37% $HCl_{aq}$. The mixture was evaporated and the residue was re-dissolved in DCM-MeOH—$NH_4OH$ (90-10-1) and evaporated. The residue was purified by flash chromatography with DCM-MeOH (9-1) to give 500 mg of the title compound. (80% yield)

MS (ES) m/z 174.2 [M+H]$^+$..

Preparation 45: 1-(4-Chloro-butyl)-4-pyridin-3-yl-1H-pyrimidin-2-one (Prep45)

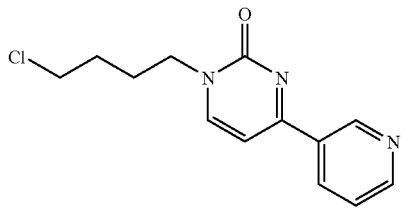

To a solution of 4-pyridin-3-yl-1H-pyrimidin-2-one (50 mg, 0.29 mmol) in dry DMF (11 ml), 60% NaH (15 mg, 0.37 mmol) was added portionwise under inert atmosphere. After heating the mixture at 100° C. for 1 hour, 1-bromo-4-chlorobutane (43 µl, 0.37 mmol) was added at room temperature and the mixture was stirred overnight. Water was added and the mixture extracted with diethyl ether to remove the dialkylated product and finally with ethyl acetate. Ethyl acetate was washed with brine, dried ($Na_2SO_4$) and evaporated to give 40 mg of the title compound as a solid (54% yield).

MS (ES) m/z 264.1 $[M+H]^+$.

Preparation 46: 4-Iodo-2-methylsulfanyl-pyrimidine (Prep46)

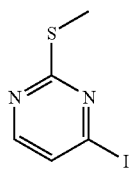

4-Chloro-2-methylsulfanyl-pyrimidine (0.75 ml, 6.2 mmol) and 57% $HI_{aq}$ (5.6 ml) were mixed and stirred at room temperature for 48 hours. The mixture was extracted with DCM and washed with a solution of $NaS_2O_3$ and then with 5% $NaHCO_3$. The organic phase was dried ($Na_2SO_4$) and evaporated, the residue was triturated with petroleum ether to give 1.30 g of the title compound that was used in the next step without further purification (83% yield).

MS (ES) m/z 253.1 $[M+H]^+$

Preparation 47: 4-(2,4-Dimethyl-thiazol-5-yl)-2-methylsulfanyl-pyrimidine (Prep47)

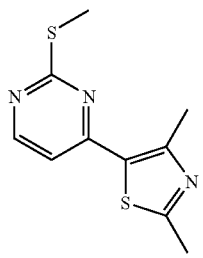

To a solution of 4-iodo-2-methylsulfanyl-pyrimidine (390 mg, 1.56 mmol), 2,4-dimethyl-5-(4,4,5,5-tetramethyl-[1,3,2] dioxaborolan-2-yl)-thiazole (633 mg, 2.65 mmol added portionwise), $Na_2CO_3$ (215 mg, 2.02 mmol), triphenylphosphine (42 mg, 0.15 mmol) in nPrOH (25 ml), $Pd(OAc)_2$ (11 mg, 0.047 mmol) was added and the mixture was refluxed for 2 hour. The solvent was evaporated under vacuum, and the crude was dissolved in DCM and washed with water. The organic phase was dried ($Na_2SO_4$) and evaporated. A second batch of this compound was prepared according to the same protocol starting from 0.39 mmol of 4-iodo-2-methylsulfanyl-pyrimidine. The residues, deriving from the two batches, were purified by flash chromatography with hexane-ethyl acetate to give the title compound (352, 76% yield).

MS (ES) m/z 238.2 $[M+H]^+$.

Preparation 48: 4-(2,4-Dimethyl-thiazol-5-yl)-2-methanesulfonyl-pyrimidine (Prep48)

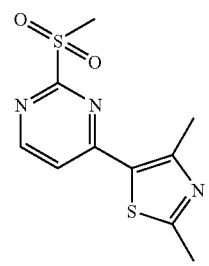

A solution of 4-(2,4-dimethyl-thiazol-5-yl)-2-methylsulfanyl-pyrimidine (342 mg, 1.44 mmol) in MeOH (12 ml) was cooled at 0° C., then an aqueous solution of oxone (2.65 g, 4.32 mmol in 12 ml of water) was slowly added. After stirring 2 hours at room temperature, the mixture was basified with 5% $NaHCO_3$ and the product was extracted with ethyl acetate. The organic phase was dried ($Na_2SO_4$) and evaporated to give 288 mg of the title compound that was used in the next step without further purification (75% yield).

MS (ES) m/z 270.3 $[M+H]^+$.

Preparation 49: 4-(2,4-Dimethyl-thiazol-5-yl)-1H-pyrimidin-2-one (Prep49)

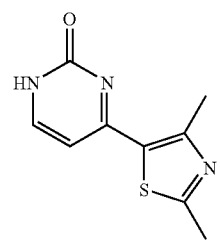

4-(2,4-dimethyl-thiazol-5-yl)-2-methanesulfonyl-pyrimidine (288 mg, 1.07 mmol) was dissolved in dioxane (13 ml) and then 2N $NaOH_{aq}$ (6 ml, 12 mmol) was added. After stirring at room temperature for 1 hour, the solution was acidified with 37% $HCl_{aq}$. The mixture was evaporated and the residue was purified by flash chromatography with DCM-MeOH (9-1) to give 166 mg of the title compound. (75% yield)

MS (ES) m/z 208.2 $[M+H]^+$..

Preparation 50: 1-(4-Chloro-butyl)-4-(2,4-dimethyl-thiazol-5-yl)-1H-pyrimidin-2-one (Prep50)

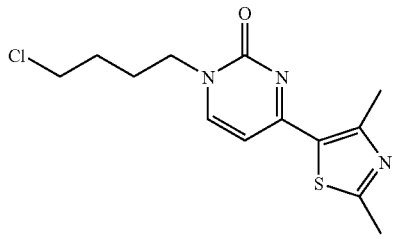

To a solution of 4-(2,4-Dimethyl-thiazol-5-yl)-1H-pyrimidin-2-one (120 mg, 0.58 mmol) in dry DMF (21 ml), 60% NaH (24 mg, 0.75 mmol) was added portionwise under inert atmosphere. After heating the mixture at 100° C. for 1 hour, 1-bromo-4-chloro-butane (86 µl, 0.75 mmol) was added at room temperature and the mixture was stirred overnight then was heated at 69° C. for 2 hours. Water was added and the mixture extracted with diethyl ether to remove the dialkylated product and finally with ethyl acetate. Ethyl acetate was washed with brine, dried ($Na_2SO_4$) and evaporated to give 80 mg of the title compound as a solid (48% yield).

MS (ES) m/z 298.1 $[M+H]^+$.

Preparation 51: 1-(4-chlorobutyl)-5-phenyl-2(1H)-pyrimidinone (Prep51)

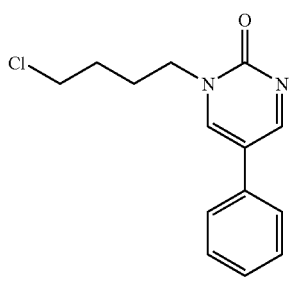

To a suspension of 5-phenyl-2(1H)-pyrimidinone (77 mg, 0.45 mmol, Aurora Screening Library or MDPI Product List or ref Helv. Chim. Acta, 10, 1927, 305//Collect. Czech. Chem. Commun., 61, 3, 1996, 458-477) in dry dichloromethane (4.0 ml), triethylamine (0.062 ml, 0.45 mmol) was added. The reaction mixture was stirred at room temperature for 30', then 1-bromo-4-chlorobutane (0.052 ml, 0.44 mmol) was added and the reaction mixture was then heated at 40° C. for 24 hours and other 24 hours at 60° C. Water (22 ml) was added to the cold mixture and the organic layers were extracted with DCM (3×10 ml). The organic layers were combined and dried over $Na_2SO_4$, filtered and concentrated in vacuo. The crude product was purified by column chromatography on silica gel eluting with DCM/methanol 96/4 to afford the title compound (60 mg, 51%).

$^1$H-NMR (CHLOROFORM-d) δ ppm 8.81-8.94 (m, 1H) 7.82-7.91 (m, 1H) 7.35-7.59 (m, 5H) 4.03 (t, 2H) 3.61 (t, 2H) 1.99-2.12 (m, 2H) 1.80-1.96 (m, 2H)

Example 1

4-phenyl-1-(4-{(1S,5R)-1-[4-(trifluoromethyl)phenyl]-3-azabicyclo[3.1.0]hex-3-yl}butyl)-2(1H)-pyrimidinone hydrochloride (E1)

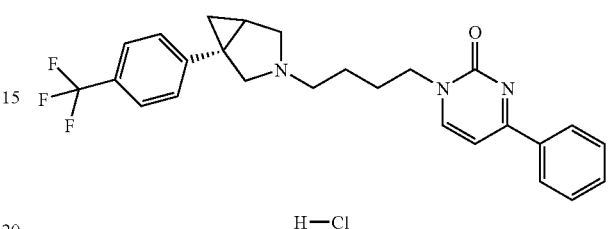

A mixture of 1-(4-chlorobutyl)-4-phenyl-2(1H)-pyrimidinone (Prep5, 52 mg), (1S,5R)-1-[4-(trifluoromethyl)phenyl]-3-azabicyclo[3.1.0]hexane (Prep4, 30 mg), $K_2CO_3$ (36 mg) and NaI (33 mg) in DMF (anhydrous, 0.5 mL) was heated at 70° C. for 18 h. After elimination of the solvent under reduced pressure, the residue was dissolved in EtOAc and the organic layer was washed with water and dried over $Na_2SO_4$. This solution was filtered and the filtrate was concentrated in vacuo. The crude was purified by flash chromatography (dichloromethane to 5% MeOH/0.5% $NH3_{acq}$ in DCM) to give 45 mg of the free base of the title compound. To a solution of this material in DCM (0.2 mL) was added 0.1 mmol of HCl (1M solution in $Et_2O$), the solvent evaporated under vacuo and the material obtained triturated with $Et_2O$ to give 40 mg of the title compound as a white slightly hygroscopic solid (62% yield).

1H NMR (DMSO-$d_6$) ppm 1.16-1.23 (m, 1H) 1.62-1.68 (m, 1H) 1.69-1.79 (m, 4H) 2.25-2.32 (m, 1H) 3.19-3.28 (m, 2H) 3.46-3.54 (m, 1H) 3.60-3.66 (m, 1H) 3.70 (dd, 1H) 3.89-3.94 (m, 2H) 4.04 (dd, 1H) 7.12 (d, 1H) 7.48 (d, 2H) 7.53 (t, 2H) 7.55-7.61 (m, 1H) 7.70 (d, 2H) 8.12 (d, 2H) 8.32 (d, 1H) 10.27 (br. s., 1H). MS (m/z): 491$[MH]^+$.

Example 2

4-methyl-1-(4-{(1S,5R)-1-[4-(trifluoromethyl)phenyl]-3-azabicyclo[3.1.0]hex-3-yl}butyl)-3,4-dihydro-2(1H)-pyrimidinone hydrochloride (E2)

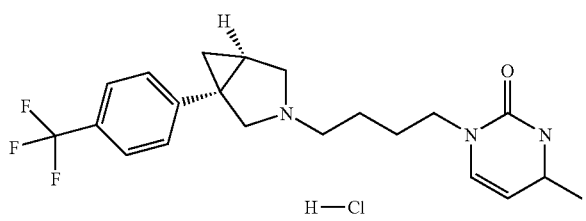

The title compound was prepared using a similar procedure as set out earlier in Example 1, from (1S,5R/1R,5S)-1-(4-(trifluoromethyl)phenyl)-3-azabicyclo[3.1.0]hexane (Prep4, 40 mg) and 1-(4-chlorobutyl)-4-methyl-2(1H)-pyrimidinone (Prep6, 52 mg) heating at 90° C. for 18 h, in 36 mg yield as a white slightly hygroscopic solid.

¹H NMR (DMSO-d6) ppm 1.15-1.30 (m, 1H) 1.52-1.85 (m, 5H) 2.17-2.38 (m, 1H) 2.29 (s, 3H) 3.09-3.47 (m, 2H) 3.45-3.57 (m, 1H) 3.59-3.69 (m, 1H) 3.67-3.77 (m, 1H) 3.80-3.91 (m, 2H) 3.98-4.10 (m, 1H) 6.40 (d, 1H) 7.49 (d, 2H) 7.72 (d, 2H) 8.12 (d, 1H) 10.24 (br. s., 1H). MS (m/z): 392[MH]⁺.

Example 3

5-methyl-4-(3-pyridinyl)-1-(4-{(1S,5R)-1-[4-(trifluoromethyl)phenyl]-3-azabicyclo[3.1.0]hex-3-yl}butyl)-2(1H)-pyrimidinone hydrochloride (E3)

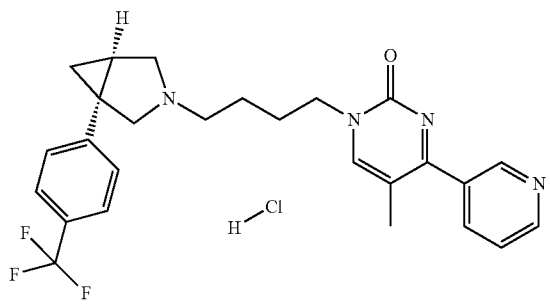

A solution of 1-(4-chloro-butyl)-5-methyl-4-pyridin-3-yl-1H-pyrimidin-2-one (Prep12, 86 mg, 0.31 mmol), (1S,5R)-1-(4-trifluoromethyl-phenyl)-3-aza-bicyclo[3.1.0]hexane (Prep4, 63 mg, 0.28 mmol), KI (2 mg) and K₂CO₃ (43 mg, 0.31 mmol) in DMF (2 ml) was placed in a microwave oven and irradiated at 115° C. for 1 hour. After cooling, the solution was diluted with water and extracted with ethyl acetate. The organic layer was washed with brine, dried (Na₂SO₄) and evaporated The solvent was removed under vacuum and the residue was redissolved in DCM and filtered, the filtrate was stirred in the presence of PS-isocyanate (350 mg) for 3 hours. The mixture was filtered and the solvent removed under vacuum. The crude was purified by flash chromatography with DCM-MeOH—NH₄OH (99-1-0.1) to give the title compound (17 mg, 4% yield) as a free base.

5-Methyl-4-pyridin-3-yl-1-[4-((1S,5R)-1-p-tolyl-3-azabicyclo[3.1.0]hex-3-yl)-butyl]-1H-pyrimidin-2-one was treated with 4N HCl in dioxane (1 eq), to give the title compound.

MS (ES) m/z 469.2 [M+H]⁺.

¹H-NMR (DMSO-d₆, TFA, 300 MHz) δ: 11.07 (br. s., 1H), 9.00 (s, 1H), 8.90 (d, 1H), 8.44 (s, 1H), 8.46 (d, 1H), 7.90 (dd, 1H), 7.70 (m, 2H), 7.50 (m, 2H), 4.03 (dd, 1H), 3.95 (t, 2H), 3.58-3.75 (m, 2H), 3.44-3.56 (m, 1H), 3.18-3.35 (m, 2H), 2.21-2.36 (m, 1H), 2.10 (s, 3H), 1.90 (dd, 0H), 1.70-1.87 (m, 4H), 1.18 (dd, 1H)

Example 4

4-(6-methyl-2-pyridinyl)-1-(4-{(1S,5R)-1-[4-(trifluoromethyl)phenyl]-3-azabicyclo[3.1.0]hex-3-yl}butyl)-2(1H)-pyrimidinone dihydrochloride (E4)

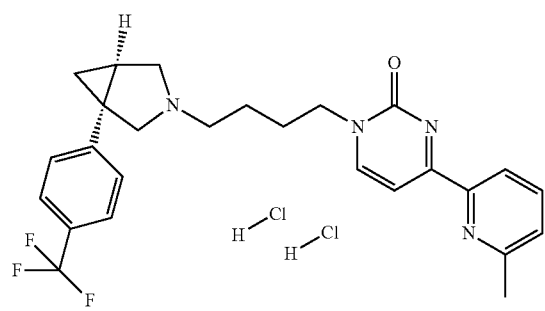

A solution of 1-(4-chloro-butyl)-4-(6-methyl-pyridin-2-yl)-1H-pyrimidin-2-one (Prep17, 48 mg, 0.17 mmol), (1S, 5R)-1-(4-trifluoromethyl-phenyl)-3-aza-bicyclo[3.1.0]hexane (Prep4, 38 mg, 0.17 mmol), KI (2 mg) and DIPEA (66 mg, 0.51 mmol) in absolute EtOH (2 ml) was placed in a microwave oven and irradiated at 125° C. for 13 hours. The solvent was removed under vacuum and the residue was redissolved in DCM and filtered. The filtrate was stirred in the presence of PS-isocyanate (350 mg) for 3 hours. The mixture was filtered and the solvent removed under vacuum. The crude was purified by flash chromatography with DCM-MeOH—NH₄OH (99-1-0.1) to give the title compound (17 mg, 4% yield) as a free base.

4-(6-Methyl-pyridin-2-yl)-1-{4-[(1S,5R)-1-(4-trifluoromethyl-phenyl)-3-aza-bicyclo[3.1.0]hex-3-yl]-butyl}-1H-pyrimidin-2-one was treated with 4N HCl in dioxane (2 eq), to give the title compound.

MS (ES) m/z 469.26 [M+H]⁺.

¹H-NMR (DMSO-d₆, TFA, 300 MHz) δ: 10.30 (br. s., 1H), 8.38 (d, 1H), 8.15 (d, 1H), 7.92 (dd, 1H), 7.69 (m, 2H), 7.44-7.54 (m, 3H), 7.39 (d, 1H), 4.05 (dd, 1H), 3.86-4.01 (m, 2H), 3.59-3.80 (m, 2H), 3.43-3.59 (m, 1H), 3.25 (br. s., 2H), 2.59 (s, 3H), 2.22-2.35 (m, 1H), 1.70-1.82 (m, 4H), 1.64 (dd, 1H), 1.20 (dd, 1H)

Example 5

4-(2,2-difluoro-1,3-benzodioxol-4-yl)-1-(4-{(1S,5R)-1-[4-(trifluoromethyl)phenyl]-3-azabicyclo[3.1.0]hex-3-yl}butyl)-2(1H)-pyrimidinone hydrochloride (E5)

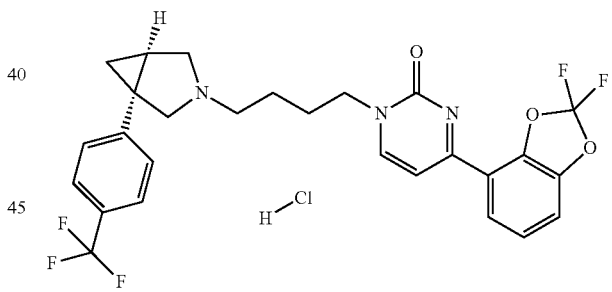

A solution of 1-(4-chloro-butyl)-4-(2,2-difluoro-benzo[1,3]dioxol-4-yl)-1H-pyrimidin-2-one (Prep22, 123 mg, 0.36 mmol), (1S,5R)-1-(4-trifluoromethyl-phenyl)-3-aza-bicyclo[3.1.0]hexane (Prep4, 81 mg, 0.36 mmol), KI (2 mg) and TEA (150 µl, 1.08 mmol) in absolute EtOH (4 ml) was heated at 90° C. for 48 hours. The solvent was removed under vacuum and the residue was redissolved in DCM and stirred in the presence of PS-isocyanate for 2 hours. The mixture was filtered and the solvent removed under vacuum. The crude was finally purified by preparative LC-MS. The so obtained trifluoroacetate salt was passed over SCX cartridge affording 46 mg of free base of the title compound (24% yield).

4-(2,2-Difluoro-1,3-benzodioxol-4-yl)-1-{4-[(1S,5R)-1-(4-trifluoromethyl-phenyl)-3-aza-bicyclo[3.1.0]hex-3-yl]-butyl}-1H-pyrimidin-2-one was treated with 4N HCl in dioxane (1 eq), to give the title compound.

MS (ES) m/z 534.24 [M+H]⁺.

¹H-NMR (DMSO-d₆, TFA, 300 MHz) δ: 10.46 (br. s., 1H), 8.40 (d, 1H), 7.88 (dd, 1H), 7.69 (m, 2H), 7.62 (dd, 1H), 7.49 (m, 2H), 7.37 (dd, 1H), 6.97 (d, 1H), 4.05 (dd, 1H), 3.90-4.00 (m, 2H), 3.59-3.81 (m, 2H), 3.41-3.59 (m, 1H), 3.19-3.31 (m, 2H), 2.16-2.31 (m, 1H), 1.76 (br. s., 4H), 1.65-1.73 (m, 1H), 1.09-1.32 (m, 1H).

Example 6

4-(2-methyl-3-pyridinyl)-1-(4-{(1S,5R)-1-[4-(trifluoromethyl)phenyl]-3-azabicyclo[3.1.0]hex-3-yl}butyl)-2(1H)-pyrimidinone hydrochloride (E6)

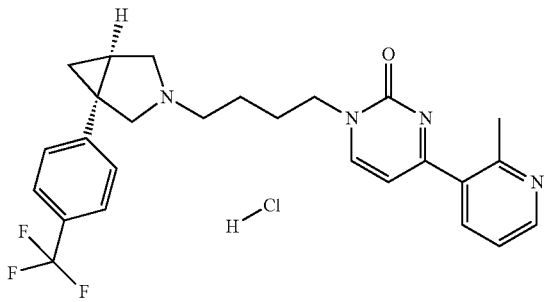

A solution of 1-(4-chloro-butyl)-4-(2-methyl-pyridin-3-yl)-1H-pyrimidin-2-one (Prep27, 161 mg, 0.58 mmol), (1S, 5R)-1-(4-trifluoromethyl-phenyl)-3-aza-bicyclo[3.1.0]hexane (Prep4, 132 mg, 0.58 mmol), and K₂CO₃ (79 mg, 0.58 mmol) in DMF (4 ml) was placed in a microwave oven and heated at 120° C. for 90 minutes. The solvent was removed under vacuum and the residue was redissolved in ethyl acetate and washed with water. The organic layers was dried (Na₂SO₄) and evaporated. The crude was purified by preparative LC-MS. The so obtained trifluoroacetate salt was passed over SCX cartridge to afford 20 mg of the title compound (7% yield) as a free base.

4-(2-Methyl-pyridin-3-yl)-1-{4-[(1S,5R)-1-(4-trifluoromethyl-phenyl)-3-aza-bicyclo[3.1.0]hex-3-yl]-butyl}-1H-pyrimidin-2-one was treated with 4N HCl in dioxane (1 eq), to give the title compound.

MS (ES) m/z 469.26 [M+H]⁺.

¹H-NMR (DMSO-d₆, TFA, 300 MHz) δ: 10.95 (br. s., 1H), 8.85 (dd, 1H), 8.42-8.58 (m, 2H), 7.92 (dd, 1H), 7.70 (m, 2H), 7.50 (m, 2H), 6.85 (d, 1H), 4.04 (dd, 1H), 3.92-4.00 (m, 2H), 3.58-3.78 (m, 2H), 3.42-3.56 (m, 1H), 3.12-3.33 (m, 2H), 2.81 (s, 3H), 2.18-2.38 (m, 1H), 1.65-1.92 (m, 5H), 1.11-1.23 (m, 1H).

Example 7

4-(2-methyl-4-pyridinyl)-1-(4-{(1S,5R)-1-[4-(trifluoromethyl)phenyl]-3-azabicyclo[3.1.0]hex-3-yl}butyl)-2(1H)-pyrimidinone hydrochloride (E7)

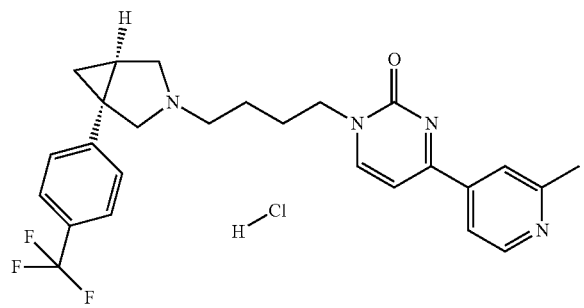

A solution of 1-(4-chloro-butyl)-4-(2-methyl-pyridin-4-yl)-1H-pyrimidin-2-one (Prep31, 100 mg, 0.36 mmol), (1S, 5R)-1-(4-trifluoromethyl-phenyl)-3-aza-bicyclo[3.1.0]hexane (Prep4, 78 mg, 0.34 mmol), KI (3 mg) and K₂CO₃ (52 mg, 0.38 mmol) in DMF (1.5 ml) was placed in a microwave oven and heated at 120° C. for 90 minutes. Water was added and the product was extracted with ethyl acetate. The organic layers was washed with brine, dried (Na₂SO₄) and evaporated. The crude was purified by preparative HPLC. The so obtained trifluoroacetate salt was passed over SCX cartridge to afford 70 mg of the title compound (41% yield) as a free base.

4-(2-Methyl-pyridin-4-yl)-1-{4-[(1S,5R)-1-(4-trifluoromethyl-phenyl)-3-aza-bicyclo[3.1.0]hex-3-yl]-butyl}-1H-pyrimidin-2-one was treated with 4N HCl in dioxane (1 eq), to give the title compound.

MS (ES) m/z 469.12 [M+H]⁺.

¹H-NMR (DMSO-d₆, TFA, 300 MHz) δ: 11.35 (br. s., 1H), 8.73 (d, 1H), 8.47 (d, 1H), 8.14 (s, 1H), 8.05 (d, 1H), 7.67 (m, 2H), 7.51 (m, 2H), 7.13 (d, 1H), 3.88-4.18 (m, 3H), 3.64 (br. s., 3H), 3.09-3.35 (m, 2H), 2.71 (s, 3H), 2.17-2.31 (m, 1H), 2.01 (t, 1H), 1.84 (br. s., 4H), 1.11-1.24 (m, 1H).

$[\alpha]^{20}_D$-37.8 (c=0.45, MeOH)

Example 8

4-(3,5-dimethyl-4-isoxazolyl)-1-(4-{(1S,5R)-1-[4-(trifluoromethyl)phenyl]-3-azabicyclo[3.1.0]hex-3-yl}butyl)-2(1H)-pyrimidinone hydrochloride (E8)

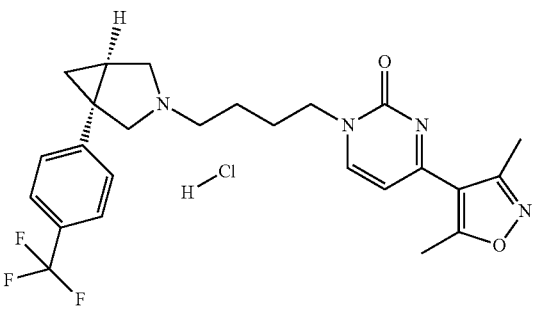

A solution of 1-(4-chloro-butyl)-4-(3,5-dimethyl-isoxazol-4-yl)-1H-pyrimidin-2-one (Prep36, mg, 0.28 mmol), (1S,5R)-1-(4-trifluoromethyl-phenyl)-3-aza-bicyclo[3.1.0]hexane (Prep4, 53 mg, 0.23 mmol) and K₂CO₃ (40 mg, 0.28 mmol) in DMF (2.5 ml) was placed in a microwave oven and heated at 120° C. for 2 hours. Water was added and the product was extracted with ethyl acetate. The organic layers was washed with brine, dried (Na₂SO₄) and evaporated. A second batch of this compound was prepared according to the same protocol starting from 0.19 mmol of 1-(4-chloro-butyl)-4-(3,5-dimethyl-isoxazol-4-yl)-1H-pyrimidin-2-one. The residues, deriving from the two batches were purified by preparative LC-MS. The so obtained trifluoroacetate salt was passed over SCX cartridge to afford title compound as a free base. 4-(3,5-Dimethyl-isoxazol-4-yl)-1-[4-((1S,5R)-1-p-tolyl-3-aza-bicyclo[3.1.0]hex-3-yl)-butyl]-1H-pyrimidin-2-one was treated with 4N HCl in dioxane (1 eq), to give 10 mg of the title compound (4% yield).

MS (ES) m/z 473.17 [M+H]⁺.

¹H-NMR (DMSO-d₆, TFA, 300 MHz) δ: 10.94 (br. s., 1H), 8.31 (d, 1H), 7.70 (m, 2H), 7.49 (m, 2H), 6.65 (d, 1H), 4.03 (dd, 1H), 3.84-3.95 (m, 2H), 3.58-3.74 (m, 3H), 3.18-3.28 (m, 2H), 2.64 (s, 3H), 2.41 (s, 3H), 2.23-2.32 (m, 1H), 1.84-1.90 (m, 1H), 1.66-1.84 (m, 4H), 1.07-1.26 (m, 1H)

Example 9

4-(2-fluorophenyl)-1-(4-{(1S,5R)-1-[4-(trifluoromethyl)phenyl]-3-azabicyclo[3.1.0]hex-3-yl}butyl)-2(1H)-pyrimidinone hydrochloride (E9)

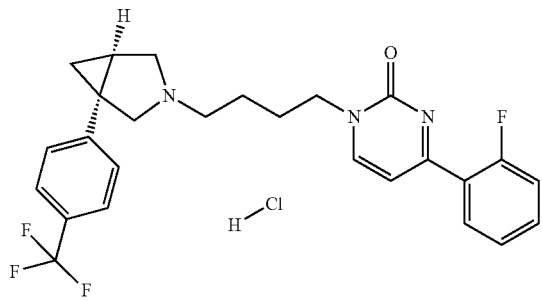

4-[4-(2-Fluoro-phenyl)-2-oxo-2H-pyrimidin-1-yl]-butyraldehyde (Prep41, 50 mg, 0.19 mmol) was dissolved in DCE (5.5 ml). The resulting solution was cooled at 0° C. and then (1S,5R)-1-(4-trifluoromethyl-phenyl)-3-aza-bicyclo[3.1.0]hexane (Prep4, 53 mg, 0.23 mmol), AcOH (13 μl) and NaBH(AcO)₃ (45 mg, 0.21 mmol) were added. The mixture was stirred for 10 minutes at 0° C. 1N NaOH_aq was added and the product was extracted with DCM. The organic phase was dried (Na₂SO₄) and evaporated. The crude was purified by flash chromatography with DCM-MeOH—NH₄OH (20-0.2-0.2) to give 52 mg of the title compound (58% yield) as a free base.

4-(2-Fluoro-phenyl)-1-{4-[(1S,5R)-1-(4-trifluoromethyl-phenyl)-aza-bicyclo[3.1.0]hex-3-yl]-butyl}-1H-pyrimidin-2-one was dissolved in dioxane and treated with 4N HCl in dioxane (1 eq), to give after trituration with iPr₂O, the title compound as a powder.

MS (ES) m/z 472.08 [M+H]⁺.

¹H-NMR (DMSO-d₆, TFA, 300 MHz) δ: 11.02 (br. s., 1H), 8.37 (d, 1H), 7.94 (td, 1H), 7.69 (m, 2H), 7.57-7.66 (m, 1H), 7.49 (m, 2H), 7.29-7.43 (m, 2H), 6.86 (dd, 1H), 3.99-4.04 (m, 1H), 3.88-3.97 (m, 2H), 3.45-3.77 (m, 3H), 3.09-3.32 (m, 1H), 2.11-2.39 (m, 1H), 1.89 (dd, 1H), 1.68-1.85 (m, 4H), 1.17 (dd, 1H).

[α]²⁰_D -38.2 (c=0.315, MeOH)

Example 10

4-(3-pyridinyl)-1-(4-{(1S,5R)-1-[4-(trifluoromethyl)phenyl]-3-azabicyclo[3.1.0]hex-3-yl}butyl)-2(1H)-pyrimidinone hydrochloride (E10)

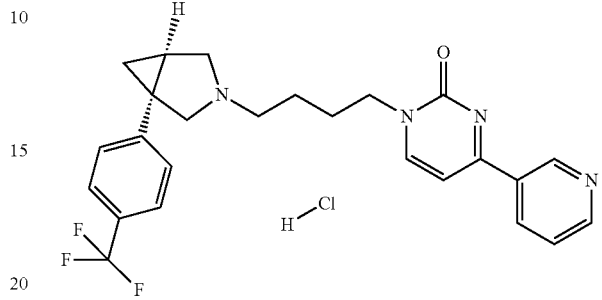

A solution of 1-(4-chloro-butyl)-4-pyridin-3-yl-1H-pyrimidin-2-one (Prep45, 38 mg, 0.14 mmol), (1S,5R)-1-(4-trifluoromethyl-phenyl)-3-aza-bicyclo[3.1.0]hexane (Prep4, 29 mg, 0.13 mmol), KI (2 mg) and K₂CO₃ (20 mg, 0.14 mmol) in DMF (1 ml) was placed in a microwave oven and irradiated at 100° C. for 45 minutes. Water was added and the mixture extracted with ethyl acetate. The organic layer was dried (Na₂SO₄), filtered and evaporated. The crude was purified by preparative LC-MS. The so obtained trifluoroacetate salt was passed over SCX cartridge to afford 22 mg of the title compound (34% yield) as a free base.

4-Pyridin-3-yl-1-{4-[(1S,5R)-1-(4-trifluoromethyl-phenyl)-3-aza-bicyclo[3.1.0]hex-3-yl]-butyl}-1H-pyrimidin-2-one with 4N HCl in dioxane (1 eq), to give the title compound.

MS (ES) 455.18 m/z [M+H]⁺.

¹H-NMR (DMSO-d₆, TFA, 300 MHz) δ: 10.99 (br. s., 1H), 9.43 (br. s., 1H), 8.94 (br. s., 1H), 8.86 (d, 1H), 8.52 (d, 1H), 7.84-8.05 (m, 1H), 7.69 (m, 2H), 7.49 (m, 2H), 7.28 (d, 1H), 4.03 (dd, 1H), 3.90-3.99 (m, 2H), 3.42-3.75 (m, 3H), 3.12-3.33 (m, 1H), 2.18-2.38 (m, 1H), 1.83-1.91 (m, 1H), 1.70-1.83 (m, 4H), 1.08-1.22 (m, 1H)

Example 11

4-(2,4-dimethyl-1,3-thiazol-5-yl)-1-(4-{(1S,5R)-1-[4-(trifluoromethyl)phenyl]-3-azabicyclo[3.1.0]hex-3-yl}butyl)-2(1H)-pyrimidinone hydrochloride (E11)

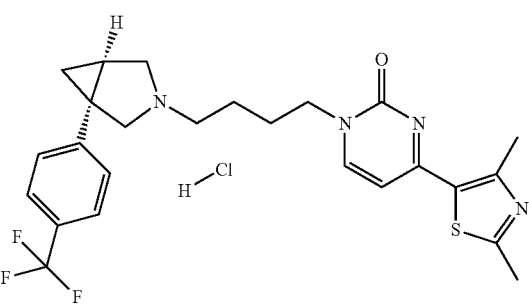

A solution of 1-(4-chloro-butyl)-4-(2,4-dimethyl-thiazol-5-yl)-1H-pyrimidin-2-one (Pre50, 80 mg, 0.27 mmol), (1S,5R)-1-(4-trifluoromethyl-phenyl)-3-aza-bicyclo[3.1.0]hexane (Pre4, 55 mg, 0.24 mmol) and $K_2CO_3$ (37 mg, 0.27 mmol) in dry DMF (2.5 ml) was placed in a microwave oven and irradiated at 115° C. for 2 hours. Water was added and the mixture extracted with ethyl acetate. The organic layer was dried ($Na_2SO_4$), filtered and evaporated. The crude was purified by preparative LC-MS. The so obtained trifluoroacetate salt was passed over SCX cartridge to afford 23 mg of the title compound (17% yield) as a free base.

4-(2,4-Dimethyl-thiazol-5-yl)-1-{4-[(1S,5R)-1-(4-trifluoromethyl-phenyl)-3-aza-bicyclo[3.1.0]hex-3-yl]-butyl}-1H-pyrimidin-2-one was treated with 4N HCl in dioxane (1 eq), to give the title compound.

MS (ES) 489.07 m/z $[M+H]^+$.

$^1$H-NMR (DMSO-$d_6$, TFA, 300 MHz) δ: 10.79 (br. s., 1H), 8.29 (d, 1H), 7.69 (m, 2H), 7.49 (m, 2H), 6.75 (d, 1H), 4.03 (dd, 1H), 3.89 (dd, 2H), 3.56-3.76 (m, 2H), 3.43-3.56 (m, 1H), 3.14-3.29 (m, 2H), 2.64 (s, 6H), 2.19-2.36 (m, 1H), 1.58-1.90 (m, 5H), 1.09-1.28 (m, 1H)

Example 12

5-phenyl-1-(4-{(1S,5R)-1-[4-(trifluoromethyl)phenyl]-3-azabicyclo[3.1.0]hex-3-yl}butyl)-2(1H)-pyrimidinone (E12)

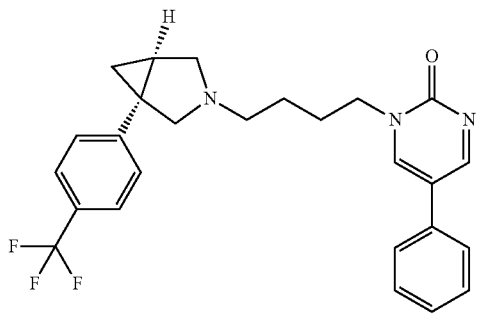

To a solution of (1S,5R)-1-[4-(trifluoromethyl)phenyl]-3-azabicyclo[3.1.0]hexane (52 mg, 0.23 mmol, prepared with a similar procedure to that reported in WO 2005080382) in N,N-dimethylformamide (DMF) (3 ml) were added at room temperature 1-(4-chlorobutyl)-5-phenyl-2(1H)-pyrimidinone (Prep51, 60.1 mg, 0.23 mmol, D1) and triethylamine (0.064 ml, 0.46 mmol). The reaction mixture was heated at 100° C. for 24 hours, then passed through a SCX cartridge (10 g) (eluting with methanol followed by 2N ammonia solution in methanol). The crude obtained was then purified by column chromatography on silica gel eluting with DCM/methanol 96/4. After evaporation of the solvent the compound recovered (20 mg, 0.044 mmol) was dissolved in DCM (1 ml) and treated with HCl (1.1 eq of a 1.25 M solution in methanol, 0.048 mmol). The resulting mixture was stirred at room temperature for 0.5 hour. Evaporation of the solvent and trituration with diethyl ether (2×3 ml) gave the hydrochloride salt of the title compound. The recovered material was passed through SCX (2 g) cartridge (eluting with methanol followed by 2N ammonia solution in methanol) to recover (6 mg, 0.013 mmol) of the title compound.

MS (ES) m/z: 454 $[MH]^+$ $^1$H-NMR(CHLOROFORM-d) δ ppm 8.89 (d, 1H) 7.82 (d, 1H) 7.54 (d, 2H) 7.38-7.51 (m, 5H) 7.22 (d, 2H) 4.03 (t, 2H) 3.27-3.48 (m, 1H) 3.04-3.21 (m, 1H) 2.39-2.71 (m, 4H) 1.86-2.01 (m, 2H) 1.71-1.83 (m, 1H) 1.46-1.65 (m, 3H) 0.77-0.92 (m, 1H)

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. Compound of formula (I)' or a salt thereof:

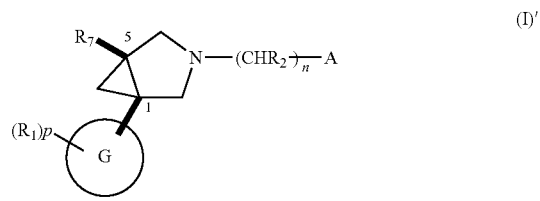

wherein
G is selected from the group consisting of: phenyl, a 5- or 6-membered monocyclic heteroaryl group, or a 8- to 11-membered heteroaryl bicyclic group;
A is a group P wherein P is

p is an integer ranging from 0 to 5;
$R_1$ is halogen, hydroxy, cyano, halo$C_{1-4}$alkyl, $C_{1-4}$alkoxy, halo$C_{1-4}$alkoxy, $C_{1-4}$alkanoyl and $SF_5$; or corresponds to a group $R_6$; and when p is an integer ranging from 2 to 5, each $R_1$ may be the same or different;
$R_2$ is hydrogen or $C_{1-4}$alkyl;
n is 4, 5 or 6;
$R_3$ is selected in the group consisting of: hydrogen, halogen, cyano, $C_{1-4}$alkyl, $C_{3-7}$ cycloalkyl, $C_{1-4}$alkoxy, halo$C_{1-4}$alkoxy, $C_{1-4}$alkanoyl and NR'R''; or $R_3$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, $C_{1-4}$alkoxy, $C_{1-4}$alkanoyl, $SF_5$ and halo$C_{1-4}$-alkoxy; and wherein such halo$C_{1-4}$alkoxy substituents, when placed in adjacent positions, may form, together with the carbon atoms to which they're attached a 5 or 6-membered unsaturated heterocyclic ring;
$R_4$ is selected in the group consisting of: hydrogen, halogen, hydroxy, cyano, $C_{1-4}$alkyl, $C_{3-7}$ cycloalkyl, $C_{1-4}$alkoxy, halo$C_{1-4}$alkoxy, $C_{1-4}$alkanoyl and NR'R'';

or $R_4$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, $C_{1-4}$alkoxy, $C_{1-4}$alkanoyl and $SF_5$;

$R_5$ is selected from the group consisting of: hydrogen, halogen, hydroxy, cyano, $C_{1-4}$alkyl, $C_{3-7}$ cycloalkyl, halo$C_{1-4}$alkyl, $C_{1-4}$alkoxy, halo$C_{1-4}$alkoxy, $C_{1-4}$alkanoyl and NR'R"; or $R_5$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl and $SF_5$;

$R_6$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such $R_6$ group is optionally substituted by one or two substituents selected from: halogen, cyano, $C_{1-4}$alkyl, $C_{1-4}$alkoxy, $C_{1-4}$alkanoyl;

$R_7$ is hydrogen or $C_{1-2}$alkyl;
R' is H, $C_{1-4}$ alkyl or $C_{1-4}$ alkanoyl;
R" is defined as R';
R' and R" taken together with the interconnecting nitrogen atom may form a 5-, 6-membered saturated or unsaturated heterocyclic ring;
wherein at least one of $R_4$ and $R_5$ is hydrogen; and wherein only one $R_2$ group may be different from hydrogen.

2. A compound of formula (IA)

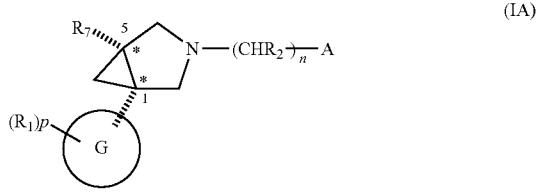

(IA)

wherein
G is selected from the group consisting of: phenyl, a 5- or 6-membered monocyclic heteroaryl group, or a 8- to 11-membered heteroaryl bicyclic group;
A is a group P wherein P is

(P)

p is an integer ranging from 0 to 5;
$R_1$ is halogen, hydroxy, cyano, halo$C_{1-4}$alkyl, $C_{1-4}$alkoxy, halo$C_{1-4}$alkoxy, $C_{1-4}$alkanoyl and $SF_5$; or corresponds to a group $R_6$; and when p is an integer ranging from 2 to 5, each $R_1$ may be the same or different;
$R_2$ is hydrogen or $C_{1-4}$alkyl;
n is 4, 5 or 6;
$R_3$ is selected in the group consisting of: hydrogen, halogen, cyano, $C_{3-7}$ cycloalkyl, $C_{1-4}$alkoxy, halo$C_{1-4}$alkoxy, $C_{1-4}$alkanoyl and NR'R"; or $R_3$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, $C_{1-4}$alkoxy, $C_{1-4}$alkanoyl, $SF_5$ and halo$C_{1-4}$alkoxy; and wherein such halo$C_{1-4}$alkoxy substituents, when placed in adjacent positions, may form, together with the carbon atoms to which they're attached a 5 or 6-membered unsaturated heterocyclic ring;

$R_4$ is selected in the group consisting of: hydrogen, halogen, hydroxy, cyano, $C_{1-4}$alkyl, $C_{3-7}$ cycloalkyl, halo$C_{1-4}$ alkyl, $C_{1-4}$alkoxy, halo$C_{1-4}$alkoxy, $C_{1-4}$alkanoyl and NR'R"; or $R_4$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl and $SF_5$;

$R_5$ is selected from the group consisting of: hydrogen, halogen, hydroxy, cyano, $C_{1-4}$alkyl, $C_{3-7}$ cycloalkyl, halo$C_{1-4}$alkyl, $C_{1-4}$alkoxy, halo$C_{1-4}$alkoxy, $C_{1-4}$alkanoyl and NR'R"; or $R_5$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl and $SF_5$;

$R_6$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such $R_6$ group is optionally substituted by one or two substituents selected from: halogen, cyano, $C_{1-4}$alkyl, halo$C_{1-4}$alkyl, $C_{1-4}$alkoxy, $C_{1-4}$alkanoyl;

$R_7$ is hydrogen or $C_{1-2}$alkyl;
R' is H, $C_{1-4}$ alkyl or $C_{1-4}$ alkanoyl;
R" is defined as R';
R' and R" taken together with the interconnecting nitrogen atom may form a 5-, 6-membered saturated or unsaturated heterocyclic ring;
wherein at least one of $R_4$ and $R_5$ is hydrogen; and wherein only one $R_2$ group may be different from hydrogen.

3. A compound according to claim 2 selected from the group consisting of:
5-phenyl-1-(4-{(1S,5R)-1-[4-(trifluoromethyl)phenyl]-3-azabicyclo[3.1.0]hex-3-yl}butyl)-2(1H)-pyrimidinone;
4-(2,4-dimethyl-1,3-thiazol-5-yl)-1-(4-{(1S,5R)-1-[4-(trifluoromethyl)phenyl]-3-azabicyclo[3.1.0]hex-3-yl}butyl)-2(1H)-pyrimidinone;
4-(3-pyridinyl)-1-(4-{(1S,5R)-1-[4-(trifluoromethyl)phenyl]-3-azabicyclo[3.1.0]hex-3-yl}butyl)-2(1H)-pyrimidinone;
4-(2-fluorophenyl)-1-(4-{(1S,5R)-1-[4-(trifluoromethyl)phenyl]-3-azabicyclo[3.1.0]hex-3-yl}butyl)-2(1H)-pyrimidinone;
4-(3,5-dimethyl-4-isoxazolyl)-1-(4-{(1S,5R)-1-[4-(trifluoromethyl)phenyl]-3-azabicyclo[3.1.0]hex-3-yl}butyl)-2(1H)-pyrimidinone;
4-(2-methyl-4-pyridinyl)-1-(4-{(1S,5R)-1-[4-(trifluoromethyl)phenyl]-3-azabicyclo[3.1.0]hex-3-yl}butyl)-2(1H)-pyrimidinone;
4-(2-methyl-3-pyridinyl)-1-(4-{(1S,5R)-1-[4-(trifluoromethyl)phenyl]-3-azabicyclo[3.1.0]hex-3-yl}butyl)-2(1H)-pyrimidinone;
4-(2,2-difluoro-1,3-benzodioxol-4-yl)-1-(4-{(1S,5R)-1-[4-(trifluoromethyl)phenyl]-3-azabicyclo[3.1.0]hex-3-yl}butyl)-2(1H)-pyrimidinone;
4-(6-methyl-2-pyridinyl)-1-(4-{(1S,5R)-1-[4-(trifluoromethyl)phenyl]-3-azabicyclo[3.1.0]hex-3-yl}butyl)-2(1H)-pyrimidinone;

5-methyl-4-(3-pyridinyl)-1-(4-{(1S,5R)-1-[4-(trifluoromethyl)phenyl]-3-azabicyclo[3.1.0]hex-3-yl}butyl)-2(1H)-pyrimidinone;

4-methyl-1-(4-{(1S,5R)-1-[4-(trifluoromethyl)phenyl]-3-azabicyclo[3.1.0]hex-3-yl}butyl)-3,4-dihydro-2(1H)-pyrimidinone;

4-phenyl-1-(4-{(1S,5R)-1-[4-(trifluoromethyl)phenyl]-3-azabicyclo[3.1.0]hex-3-yl}butyl)-2(1H)-pyrimidinone;

and salts thereof.

4. A method of treating a condition for which modulation of dopamine $D_3$ receptors is beneficial, which comprises administering to a patient in need thereof an effective amount of a compound of formula (I)' according to claim 1, neat or admixed with a pharmaceutically acceptable carrier, wherein the condition is psychosis or a psychotic condition, substance abuse or premature ejaculation.

5. A pharmaceutical composition comprising a compound of formula (I)' according to claim 1 or a pharmaceutically acceptable salt thereof admixed with a pharmaceutically acceptable carrier.

6. A method of treating a condition for which modulation of dopamine $D_3$ receptors is beneficial, which comprises administering to a patient in need thereof an effective amount of a compound of formula (IA) according to claim 2, neat or admixed with a pharmaceutically acceptable carrier, wherein the condition is psychosis or a psychotic condition, substance abuse or premature ejaculation.

7. A pharmaceutical composition comprising a compound of formula (IA) according to claim 2 or a pharmaceutically acceptable salt thereof admixed with a pharmaceutically acceptable carrier.

* * * * *